(12) United States Patent
Ervin et al.

(10) Patent No.: US 11,393,570 B2
(45) Date of Patent: *Jul. 19, 2022

(54) METHOD, SYSTEM AND APPARATUS FOR GUIDING AND TRACKING MEDICATION USAGE

(71) Applicant: MedicaSafe, Inc., New York, NY (US)

(72) Inventors: Matthew J. Ervin, New York, NY (US); Aziz O. Nawrozie, New York, NY (US); Jason P. Wright, Brooklyn, NY (US); Malcolm V. Dell, Tappan, NY (US)

(73) Assignee: MedicaSafe, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/934,552

(22) Filed: Jul. 21, 2020

(65) Prior Publication Data

US 2020/0350051 A1    Nov. 5, 2020

Related U.S. Application Data

(63) Continuation of application No. 15/962,548, filed on Apr. 25, 2018, now Pat. No. 10,755,808, which is a
(Continued)

(51) Int. Cl.
*G16H 20/13* (2018.01)
*A61J 1/03* (2006.01)
(Continued)

(52) U.S. Cl.
CPC ............. *G16H 20/13* (2018.01); *A61J 1/03* (2013.01); *A61J 7/0076* (2013.01); *A61J 7/0418* (2015.05);
(Continued)

(58) Field of Classification Search
CPC ........ G16H 20/13; G06F 19/3462; A61J 1/03; A61J 7/0076; A61J 7/0418; A61J 7/0454;
(Continued)

(56) References Cited

U.S. PATENT DOCUMENTS

| 4,787,222 A | 11/1988 | Irazoqui et al. |
| 5,552,777 A | 9/1996 | Gokcebay et al. |

(Continued)

FOREIGN PATENT DOCUMENTS

| CA | 2 536 348 A1 | 8/2006 |
| EP | 0 260 000 A2 | 3/1988 |
| WO | 2013/120029 A1 | 8/2013 |

OTHER PUBLICATIONS

International Search Report issued for corresponding International Patent Application No. PCT/US2019/026748 dated Aug. 8, 2019.
(Continued)

*Primary Examiner* — Michael Collins
(74) *Attorney, Agent, or Firm* — Myers Wolin, LLC

(57) ABSTRACT

Methods and systems are provided for tracking and guiding a patient's clinically directed medication usage. Medicaments are placed in secure passive packaging that must be unlocked to enable dispensing of a dose or a set of doses. This packaging is designed to be difficult to open manually, and instead is designed to dispense only when used in combination with an unlocking device. The unlocking device is a separate device containing electronics, mechatronics or both, to unlock and dispense from the packaging and to track and guide usage. Together, the secure container and the unlocking device track medication usage, deter an excessive rate of patient usage, and deter unauthorized access to medication.

24 Claims, 34 Drawing Sheets

Related U.S. Application Data continuation of application No. 14/673,765, filed on Mar. 30, 2015, now Pat. No. 10,073,955.

(60) Provisional application No. 61/972,167, filed on Mar. 28, 2014.

(51) Int. Cl.
| | | |
|---|---|---|
| *A61J 7/00* | (2006.01) | |
| *A61J 7/04* | (2006.01) | |
| *B65D 83/04* | (2006.01) | |
| *B65D 55/00* | (2006.01) | |

(52) U.S. Cl.
CPC ........... *A61J 7/0427* (2015.05); *A61J 7/0445* (2015.05); *A61J 7/0454* (2015.05); *B65D 55/00* (2013.01); *B65D 83/0409* (2013.01)

(58) Field of Classification Search
CPC ... A61J 7/0427; A61J 7/0445; B65D 83/0409; B65D 55/00
USPC .................................................. 700/231–244
See application file for complete search history.

(56) References Cited

U.S. PATENT DOCUMENTS

| | | | |
|---|---|---|---|
| 8,157,795 B2 | 4/2012 | Sartor et al. | |
| 9,033,039 B2 | 5/2015 | Eberhart et al. | |
| 9,033,939 B2 | 5/2015 | Eberhart et al. | |
| 9,827,030 B2 | 11/2017 | Vogt et al. | |
| 10,073,955 B2* | 9/2018 | Ervin | G16H 20/13 |
| 10,755,808 B2* | 8/2020 | Ervin | A61J 7/0445 |
| 2003/0127463 A1 | 7/2003 | Varis | |
| 2004/0039481 A1 | 2/2004 | De La Huerga | |
| 2005/0178779 A1 | 8/2005 | Wood | |
| 2006/0058724 A1* | 3/2006 | Handfield | A61J 7/0076 604/20 |
| 2006/0201963 A1 | 9/2006 | Sines et al. | |
| 2007/0186923 A1 | 8/2007 | Poutiatine et al. | |
| 2007/0227913 A1 | 10/2007 | Shoenfeld | |
| 2008/0164275 A1 | 7/2008 | Poutiatine et al. | |
| 2008/0203107 A1 | 8/2008 | Conley et al. | |
| 2012/0239186 A1 | 9/2012 | Kim | |
| 2014/0074283 A1 | 3/2014 | Blackburn | |
| 2014/0278510 A1 | 9/2014 | McLean et al. | |
| 2015/0127145 A1* | 5/2015 | Kim | G07F 17/0092 700/235 |
| 2018/0360693 A1 | 12/2018 | Schiff et al. | |

OTHER PUBLICATIONS

Written Opinion of the International Searching Authority issued for corresponding International Patent Application No. PCT/US2019/026748 dated Aug. 8, 2019.
Non-Final Office Action issued for corresponding U.S. Appl. No. 14/673,765 dated Sep. 7, 2017.
Final Office Action issued for corresponding U.S. Appl. No. 14/673,765 dated Jan. 11, 2018.
Non-Final Office Action issued for corresponding U.S. Appl. No. 15/962,548 dated Nov. 16, 2018.
Final Office Action issued for corresponding U.S. Appl. No. 15/962,548 dated May 8, 2019.
Non-Final Office Action issued for corresponding U.S. Appl. No. 15/962,548 dated Dec. 31, 2019.
The extended European search report with supplementary European search report and the European search opinion issued by the European Patent Office for corresponding European Patent Application No. 19793072.0, dated Jun. 25, 2021.

* cited by examiner

METHOD, SYSTEM AND APPARATUS FOR GUIDING AND TRACKING MEDICATION USAGE

CROSS-REFERENCE TO RELATED APPLICATIONS

This application is a continuation of U.S. patent application Ser. No. 15/962,548, filed Apr. 25, 2018, which is a continuation of U.S. patent application Ser. No. 14/673,765, filed Mar. 30, 2015, which claims the benefit of U.S. Provisional Application No. 61/972,167, filed Mar. 28, 2014, the contents of each of which are incorporated herein by reference.

BACKGROUND OF THE INVENTION

1. Field of the Invention

The present invention generally relates to the field of medicine. In particular, various embodiments relate to systems and methods for controlling access to medicaments.

2. Description of the Related Art

Many medications, especially drugs in pill form, are now regularly self-administered under little or no supervision. Self-administration of medication raises the possibility that a patient will fail to comply with directions regarding aspects such as dosage and timing. It is estimated that less than 50% of written prescriptions are taken as prescribed. Non-compliance can greatly diminish the effectiveness of the treatment as well as increase the likelihood of harm to the patient, neither being desirable. Further, non-compliance can increase healthcare costs and consume healthcare resources that could be allocated elsewhere but for the non-compliance.

Non-compliance often occurs by simple mistake or neglect, particularly when the patient is required to self-administer a complex regimen of medications. In order for a medical professional to respond with corrective action or to change the treatment regimen, it would be beneficial for the medical professional to be made aware of the patient's deviation from the prescribed usage. A co-related problem is that during a doctor visit, the patient may not be able to accurately relay medically relevant information about medicament usage and symptoms because the patient's previous actions, symptoms, and side effects are highly susceptible to the vagaries of memory.

The patient's non-compliance with a prescribed medication regimen may result in underdosing, overdosing, medication abuse and dependency, all of which typically affect a patient's overall health and, in many cases, can be life threatening. Overuse of certain medications, such as painkillers, has become a major societal concern. Healthcare professionals have no acceptable tools to detect abuse patterns, to deter misuse, to limit diversion, or to optimize patient education for at-risk patients.

Physical systems have been developed to restrain patient access to medicaments to a prescribed pace, and involve the use of electronics and mechatronics in the dispensing device, components that can be relatively costly. These previous approaches are useful only if each abuse-prone prescription is delivered to the patient within a secure, abuse-resistant device or package and so the dispensing device costs, or the recycling of the dispensing device, must be included in every prescription. Such costs can prove prohibitive. Even if the device costs are amortized over multiple prescriptions, recycling may involve shipping the dispensing device back to a central facility, and return shipping costs alone can prove economically unviable if applied to every prescription.

Many medication therapies can be complemented with multidisciplinary healthcare support in the form of adjunctive therapies. For example, an evidence-based treatment approach for various mental health and pain-related conditions is known as cognitive-behavioral therapy (CBT), which can be used in conjunction with prescribed medications. Even when adjunctive therapies such as CBT are available, they are almost always administered independently from the medication treatment provided by a patient's physician. This independent treatment may have clinical goals that are incongruent to the goals of the referring physician and, furthermore, treatment progress and results may not be available to the prescribing physician in a reliable and frequent manner. An integrated care approach to medical and relevant adjunctive health services would preferably combine all treatments into a single treatment plan. However, structural healthcare barriers, such as problematic inter-multidisciplinary communications, geography, and the logistical struggle of coordinating care, have prevented optimal integration of medication therapy with adjunctive therapies.

Various embodiments of the invention described herein provide a solution that addresses one or more of the issues described above.

SUMMARY OF THE INVENTION

According to at least one embodiment, methods and systems are provided for tracking and guiding a patient's clinically directed medication usage. Medicaments are placed in secure containers that must be unlocked to enable dispensing of a dose or a set of doses. The containers need not contain electronics or powered components, and hence can be made relatively inexpensively. This "secure passive packaging" is designed to be difficult to open manually, and instead is designed to dispense only when used in combination with a "smart key". The smart key may take the form of a separate device, implemented in various embodiments with electronics, mechatronics or both, to unlock and dispense medicaments from the dumb packaging and to track and guide usage. The secure container and/or smart key can be used to track medication usage, trigger reminders in accordance with actual patient data, deter an excessive rate of patient usage, and deter unauthorized access to medication. Moreover, embodiments of the invention can be interconnected with a master system that enables automatic and regular assessment of patients.

In various embodiments the smart key is able to communicate with other systems to collect data indicative of patient health. For example, the smart key could communicate with independent healthcare devices and collect data values for the patient's blood pressure, glucose levels, or weight. In specific embodiments the smart key contains a touchscreen, or can interact with external computing or telecommunications devices to interact with the patient. Via these or other means, clinically relevant assessment questionnaires regarding the status of a patient's health can be conducted by the system. These assessments can create a clinically meaningful timeline of symptoms, side-effects and activity levels.

Various embodiments allow the data gathered, both objective and subjective, to be communicated to a master system. The master system can combine data into actionable reports for use by healthcare professionals. The reports enable a healthcare professional to better assess whether or not there is an apparent pattern of progress. If progress is less than desired, the care team can then make an evidence-based decision on whether to proceed with the therapy, supplement the therapy approach, or change the therapy regimen.

Moreover, other embodiments enable intervention in an automatic or semi-automatic manner to (a) curtail medication access when overuse is noted, (b) generate reminders when underuse is detected, and (c) communicate educational messages at relevant times, based on the subjective and objective data being gathered from the patient. Certain embodiments can include an integrated care system where psychological therapies such as cognitive behavioral therapy (CBT) are tightly integrated with dispensary components that track and guide the patient through the clinically directed medication regimen. Such integrated care embodiments produce a therapy process that reduces the risks of medication misuse while optimizing patient outcomes as a result of the therapy.

Although the various embodiments are described herein for use in a healthcare setting, it will be appreciated that the invention is not so limited. Certain aspects of the invention may, for example, have applicability in other settings, such as the monitoring of cargo, valuable items, or the monitoring of devices controlled by users prone to undesirable behavior or error.

BRIEF DESCRIPTION OF THE FIGURES

The various aspects and embodiments disclosed herein will be better understood when read in conjunction with the appended drawings, wherein like reference numerals refer to like components. For the purposes of illustrating aspects of the present application, there are shown in the drawings certain preferred embodiments. It should be understood, however, that the application is not limited to the precise arrangement, structures, features, embodiments, aspects, and devices shown, and the arrangements, structures, features, embodiments, aspects and devices shown may be used singularly or in combination with other arrangements, structures, features, embodiments, aspects and devices. The drawings are not necessarily drawn to scale and are not in any way intended to limit the scope of this invention, but are merely presented to clarify illustrated embodiments of the invention. In these drawings.

DETAILED DESCRIPTION

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

The word "exemplary" is used herein to mean "serving as an example, instance, or illustration." Any embodiment described herein as "exemplary" is not necessarily to be construed as preferred or advantageous over other embodiments. Likewise, the term "embodiments of the invention" does not require that all embodiments of the invention include the discussed feature, advantage or mode of operation.

Further, many embodiments are described in terms of sequences of actions to be performed by, for example, elements of a computing device. It will be recognized that various actions described herein can be performed by specific circuits (e.g., application specific integrated circuits (ASICs)), by program instructions being executed by one or more processors, or by a combination of both. Additionally, these sequences of actions described herein can be considered to be embodied entirely within any form of computer readable storage medium having stored therein a corresponding set of computer instructions that, upon execution, would cause an associated processor to perform the functionality described herein. Thus, the various aspects of the invention may be embodied in a number of different forms. In addition, for each of the embodiments described herein, the corresponding form of any such embodiments may be described herein as, for example, "logic configured to" perform the described action.

Figure 1:
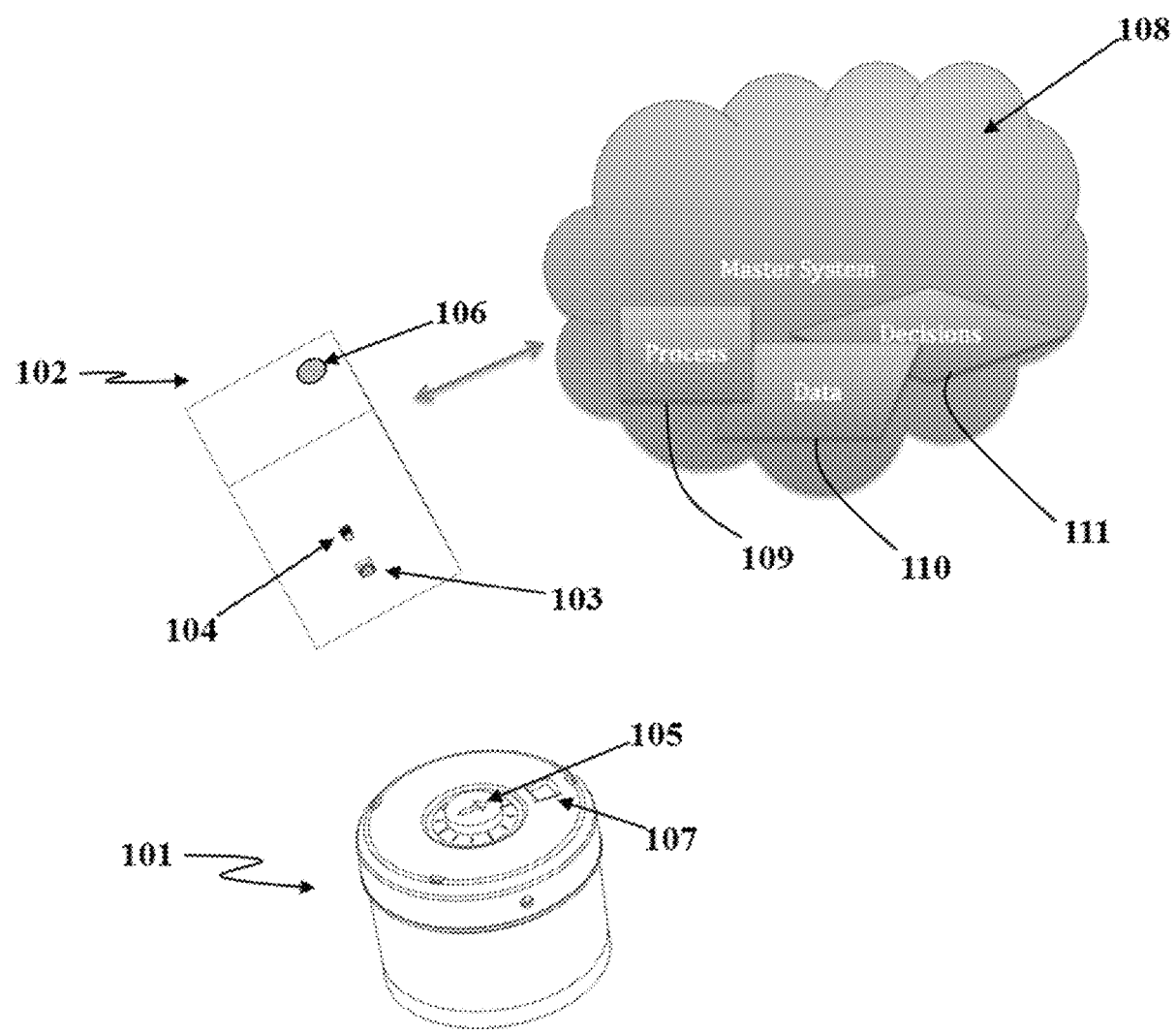
FIG. 1 is a diagram of primary system components according to one embodiment.

FIG. 1 provides an overview of an exemplary dispensing and patient guidance system. Specialized medication containers 101, referred to as pill boxes 101, are designed to be resistant to manual opening by the patient, and instead require an inconvenient or difficult process to open and dispense a pill in an unauthorized fashion. An electronic and/or mechatronic smart key 102 is designed to conduct the opening process that is otherwise difficult or inconvenient for the patient to perform. In the exemplary embodiment, the smart key 102 contains an optical reader, such as a digital camera component 103, and a motorized shaft 104 for use in dispensing medication from pill boxes 101. To dispense medications, patients place the head of the unlocking shaft 104 of the smart key 102 into an appropriate slot 105 of the pill box container 101 and then press a dispense button 106 on the smart key 102. This initiates a mechatronic process on the smart key 102 analogous to unlocking a combination lock. The successful completion of that process enables a certain quantity of medication to be removed from the pill box container 101. Each pill box 101 has a different combination that is obscured from the patient, thereby preventing patients from detecting the combination or accessing their medication when unauthorized to do so.

When smart key 102 is seated on pill box 101, the camera 103 of smart key 102 is focused on a window 107 in pill box 101 through which can be seen machine-readable indicia 601 on a top rotor 501 (shown in FIGS. 5 and 6) of pill box 101. It will be appreciated that the term "window 107" includes simply an opening in top cover 502, or an opening covered with a suitably transparent material, such as clear plastic. This indicia 601 can be barcodes, QR codes or the like, which can be decoded by the electronics of smart key 102, and smart key 102 logic that controls that unlocking shaft 104 so that top rotor 501 is turned through the necessary unlock process based on images from camera 103. Because smart key 102 is necessary for the opening process, it can be programmed to effectively control and guide the regimen. This makes possible clinically useful dispensing contingencies, such as limiting the number of pills that can be dispensed within a given time period or requiring patients to complete assessments or review educational materials as a condition for ongoing access to their medication. Once all the medications from a pill box 101 have been dispensed, pill box 101 can be disposed of. Smart key 102 can be connected to a new pill box 101 whenever desired, and can use its camera 103 to read indicia 601 describing the medication contained within.

A master system 108, capable of computing functions such as storage, process management, and logical decision-making, can have a data communication connection with smart key 102, such as via a wired or wireless communication network. Master system 108 can be either local, for example on a personal smart phone/tablet or personal computer of the user, or remote, for example on a server accessible via the Internet. The desired functions of master system 108 can also be divided between local and remote server systems, as is known in the art. Master system 108 collects usage data from smart key 102, and may communicate rules to smart key 102 that affect medication access and reminders. Master system 108 can also deliver patient-tailored instructional, assessment, and educational materials via any suitable communication means known in the art, such as: computer, phone, or via a display on smart key 102 itself. Master system 108 can control the overall therapy process 109, data collection and storage 110, and therapy decision points 111.

Figure 2:
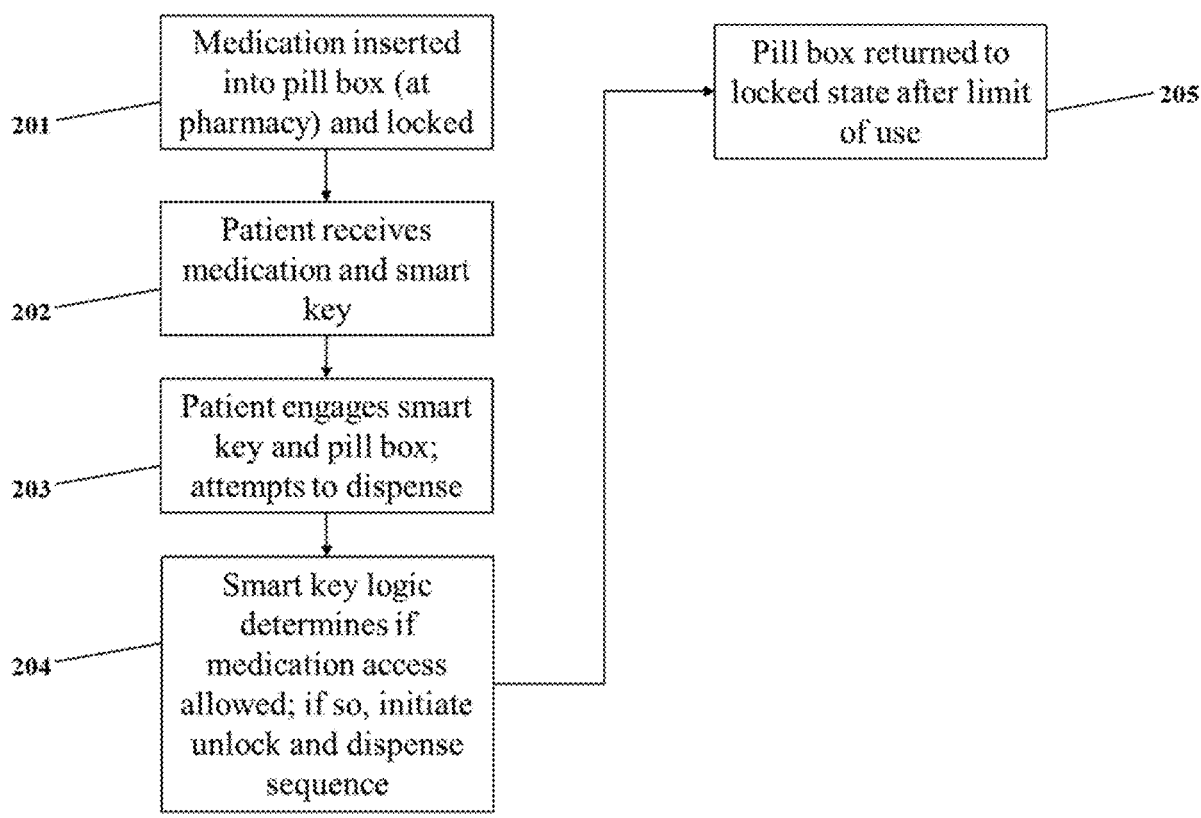
FIG. 2 is a flowchart showing an embodiment process for dispensing medications with the system illustrated in FIG. 1.

FIG. 2 illustrates the medication loading and dispensing process. Pill box containers 101 are loaded in step 201 with medications and locked (such as via a one-way snap fit) prior to delivery in step 202 to the patient. Each pill box 101 can be labeled in accordance with current FDA prescription guidelines. The exemplary pill box 101 must be unlocked via a process, like a combination lock, but the patient does not know the combination. To unlock and dispense, smart key 102 is mounted in step 203 to pill box 101, for example via a snap-unsnap temporary connection. Smart key 102 is shaped such that when it is mounted on pill box 101 the patient cannot observe the coded unlock positions being actuated by the smart key 102, and hence cannot replicate the unlock process manually. When medication is desired, the patient effects this process via smart key 102, for example by pressing a dispense button 106. Then in step 204 the smart key 102 checks internal logic and rules stored in its memory to determine if it is allowable for the patient to have access to further medication at this time. If so, smart key 102 begins the unlock sequence. Smart key 102 logs in its memory any dispensations that occur. After the patient has reached a defined limit of use for the medication, pill box 101 returns in step 205 to a locked position.

Figure 3:
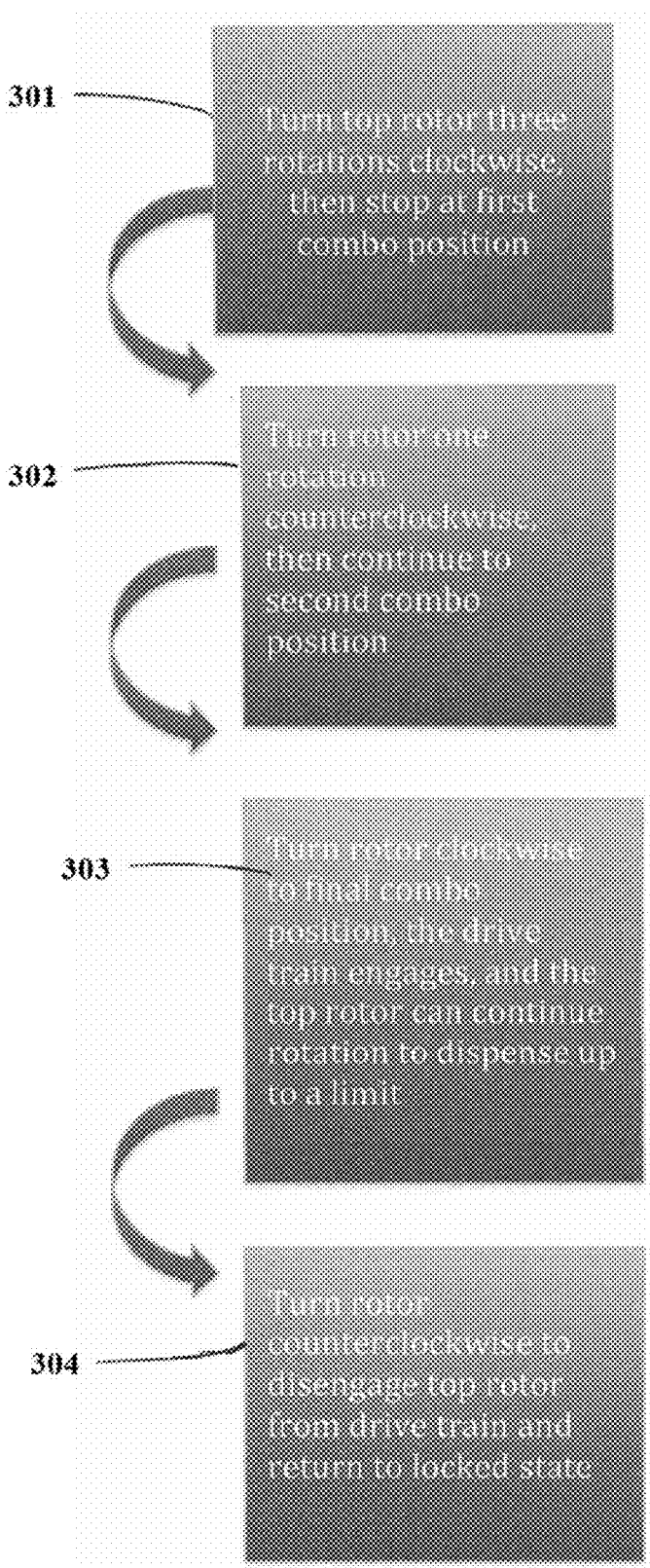
FIG. 3 is a flowchart showing a process for unlocking and dispensing from one embodiment of an access-controlled medication container.

FIG. 3 illustrates the cryptographic unlock and dispense process of the exemplary smart key 102 and pill box 101. In step 301, smart key 102 turns top rotor 501 at least three rotations clockwise, and thereafter continues the rotation until top rotor 501 reaches the position for the first number of a combination. Camera 103 of smart key 102 is used to watch machine-readable indicia 601 printed on top rotor 501, and the computing system of smart key 102 decodes these images to determine when the first position is reached, at which point a motor 410 driving shaft 104 stops. In step 302, smart key 102 turns top rotor 501 one rotation counterclockwise, continuing thereafter until it detects the second combination position via camera 103 and indicia 601 and then stops. In step 303, smart key 102 turns top rotor 501 clockwise until the camera/image system 103 detects indicia 601 on top rotor 501 that signifies the final combination position, at which point a dispensing drive train is engaged between top rotor 501 and a dispensing system that is used to dispense the medication from the pill box 101. At that point, motor 410 can turn top rotor 501 clockwise again to dispense the allowed quantity of medication. In step 304, top rotor 501 reaches a limit of motion, which coincides with a limit of medication access for that dispensing event, at which point motor 410 and top rotor 501 are reversed to disengage top rotor 501 from the underlying drive train, which effectively puts the pill box 101 back into a locked state.

Figure 4:
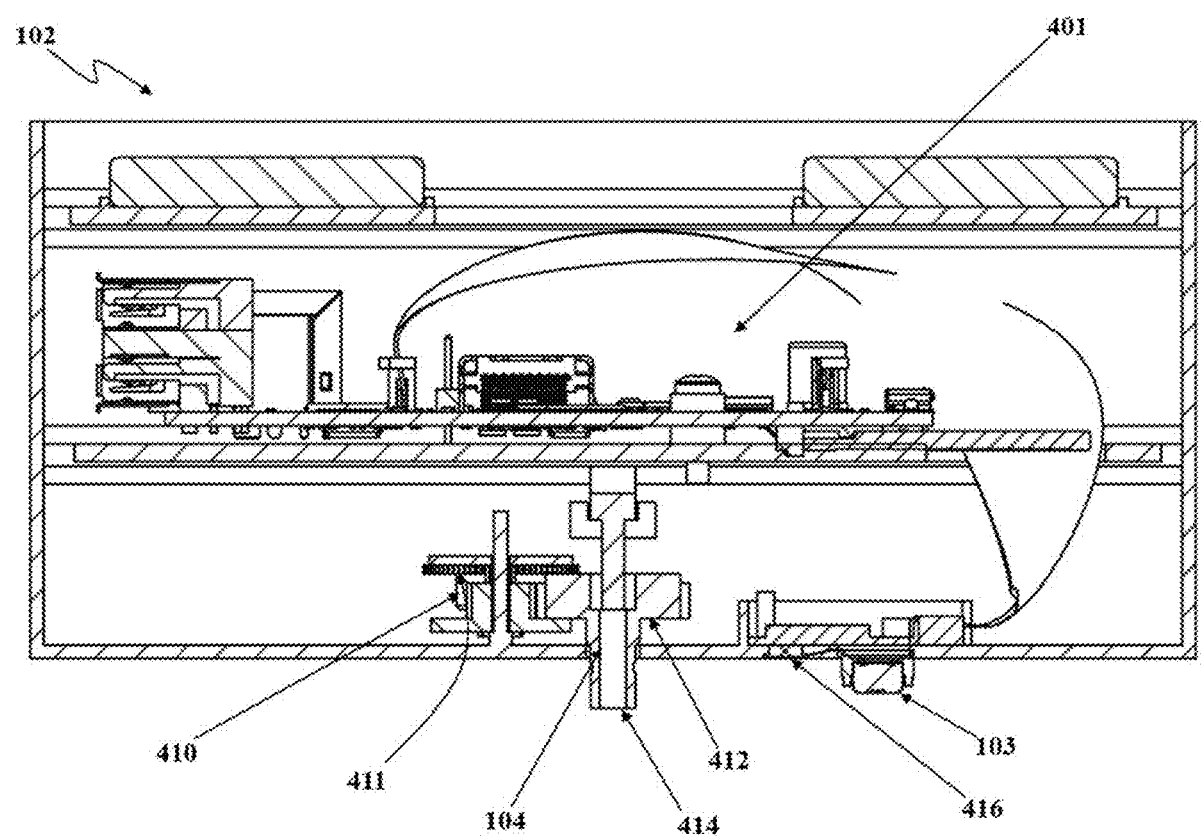
FIG. 4 is a cross-sectional view of one embodiment smart key.

FIG. 4 shows exemplary interior components of the exemplary smart key 102. A computing system 401 includes a processor, memory, storage, a battery power system, and a wireless subsystem communicating over any of a number of multiple wireless protocols or systems. The computing system 401 can also include other components known in the art of mobile or fixed computing systems. Collectively, these components form a computing system 401 which can communicate with sensors and drive and control mechatronic components. The exemplary smart key 102 uses a single board computer (SBC) as the computing system 401, which in the exemplary embodiment is a Raspberry Pi system. The SBC 401 also controls a small DC motor 410 with a gear train 411 and receives input from a potentiometer 412, and the motorized system has an external shaft 104 on which is mounted a head 414 which can fit into and rotate top rotor 501 on pill box 101 container. Computing system 401 is also optionally connected to sensors which detect when smart key 102 has been properly connected to a pill box 101 container, such as micro-switches, opto-switches or the like. SBC 401 also takes input from camera 103, which can be assisted by lights 416 mounted nearby. In the exemplary embodiment 102, SBC 401 collects and processes images from camera 103. SBC 401 runs software that can recognize and decode machine-readable indicia 601 if visible in the captured image. When a smart key 102 is connected to a pill box 101, smart key 102 will attempt to read barcodes 601 or the like on top rotor 501 of pill box container 101 via window 107. Computing system 401 can control motor 410 to rotate a pill box 101 rotor 501, which will bring different barcodes 601 into view for camera 103 as rotor 501 revolves. The control logic of SBC 401 uses input from potentiometer 412 to deduce the position of motor 410, and uses machine-readable indicia 601 to confirm the position to which motor 410 has moved top rotor 501.

Users are informed of the state of smart key 102 via LEDs or a screen provided on smart key 102. SBC 401 can further include supporting circuitry for relaying signals between SBC 401 and other system components. This circuitry can include subsystems such as an H-bridge connected to motor 410 and allowing motor 410 to be rotated in either direction. And SBC 401 is also preferably connected to a subsystem including an analog-to-digital converter connected to potentiometer 412, which is in turn connected to motor shaft 104, so that smart key 102 control software can be aware of the position of shaft 104 or motor 410 and send control signals accordingly to drive motor 410 in a desired manner.

SBC 401 optionally includes subsystems for wireless communications. This can include technology for short-range or long-range wireless communication with other system components, including support for standards known to those in the art of mobile computing, including Bluetooth, Wifi, or cellular data protocols, such as 2G, 3G, 4G, LTE, etc. Optionally, SBC 401 can be connected, directly or via a wired protocol, to an electronic screen and/or input device to communicate information to the user or accept input from the user.

Variations on the exemplary smart key 102 embodiment can includes those that have multiple motors 410 and corresponding drive shafts 104 and multiple cameras 103, features which may be used to unlock variations of the exemplary pill box. Cameras 103 can be optionally complemented by lighting systems 416, such as ultraviolet (UV) lighting components so that the camera 103 can view images that are not visible to the naked eye.

Smart key 102 preferably logs each time it is used to unlock a pill box 101. Because smart key 102 contains a computing system 401, it can be programmed to provide or not provide additional access to medication according to a set of dispensing rules crossed-referenced with dispensing data stored in its memory. For example, the dispensing rules can include a minimum duration between dosages of the medication, and thus a minimum duration between successive unlock operations. Smart key 102 can also communicate with master system 108 to communicate activity and receive updates to its operating and/or dispensing rules. Pill box containers 101 can be disposed of when empty. The ability to construct pill box 101 containers out of materials of relatively low costs is a significant advantage of various embodiments of the invention.

Figure 5:
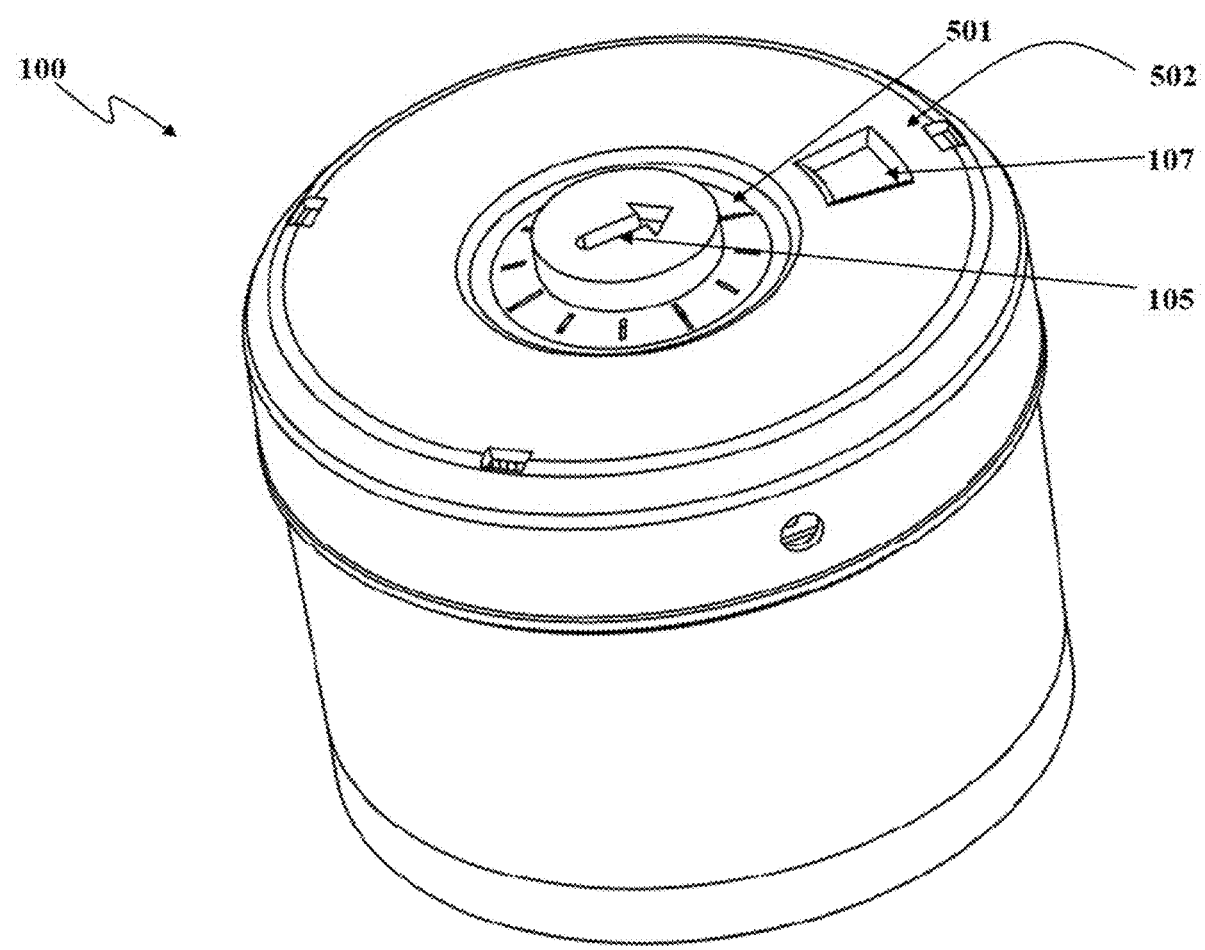
FIG. 5 is a perspective view of one embodiment of a pill box.

The exterior of exemplary pill box 101 is shown in FIG. 5. Top rotor 501, a disc shaped object, is sandwiched underneath a top cover 502 and can rotate freely thereunder. Top rotor 501 has machine-readable indicia 601 (shown in FIG. 6), such as 2D barcodes, printed on it in a ring-shaped pattern, and each indicia 601 can be selectively made visible through window 107 (which includes clear sections) of top cover 502. Indicia 601 can be printed using UV material so that they are not visible to the naked eye, but can be visible to a smart key 102 appropriately configured with UV lights 416 and/or sensors. The center of top rotor 501 has a slot 105 into which shaft head 414 from smart key 102 can enter to turn top rotor 501.

Figure 6:
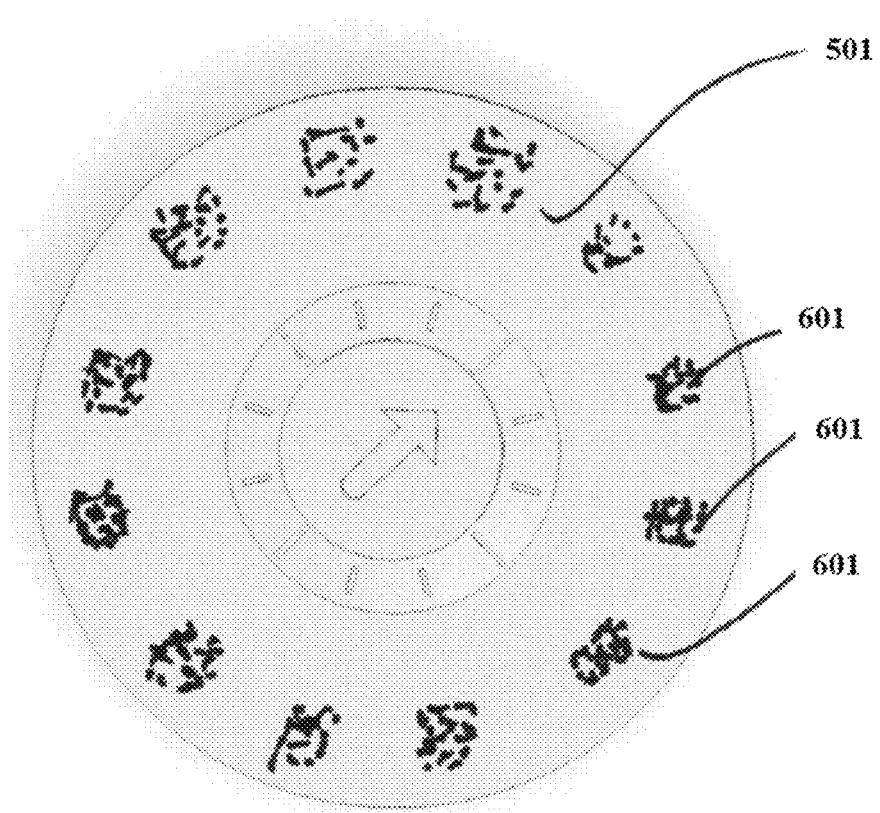
FIG. 6 is a top view of an embodiment rotor.

FIG. 6 shows top rotor 501 alone from above, with the positions of indicia 601 radially outward from each hash mark and therefore visible through window 107 of top cover 502 as top rotor 501 spins.

Figure 7:
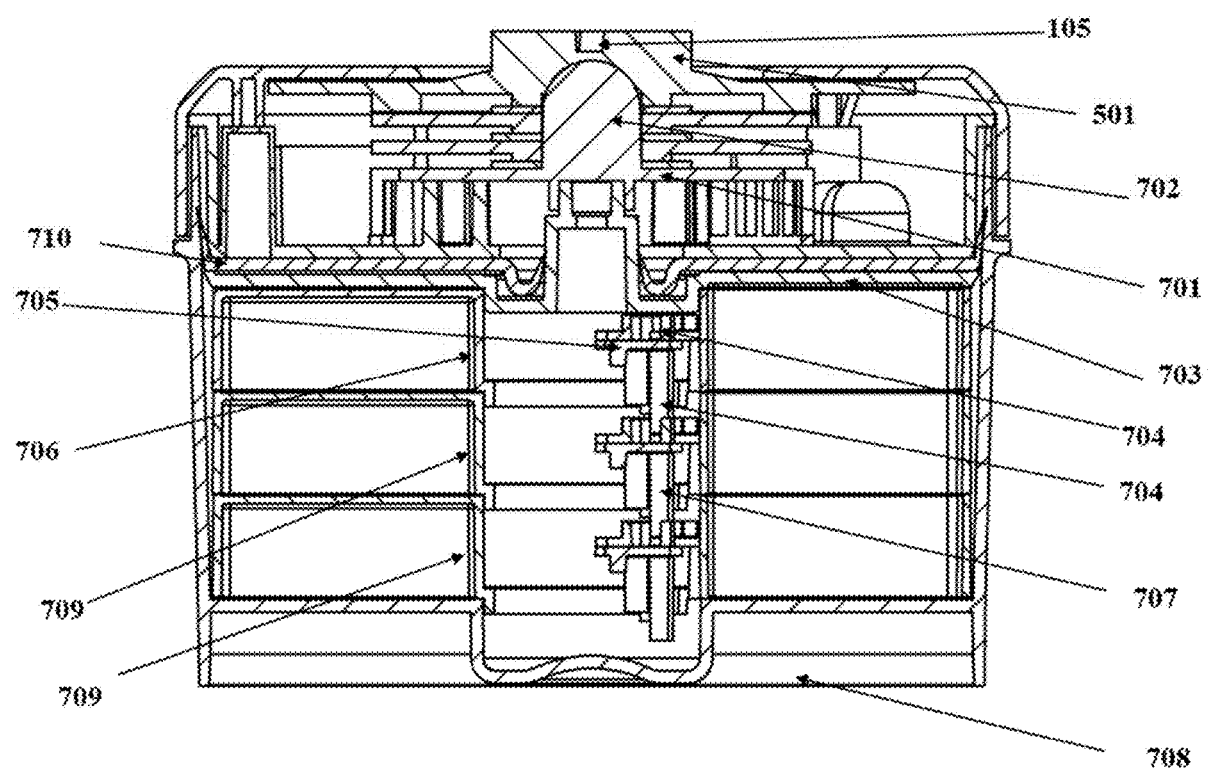
FIG. 7 is a cross-sectional view of components of an embodiment pill box.

FIG. 7 shows a cross-section of selected components of the exemplary pill box 101. Top rotor 501 can be seen in profile, including indent 105 for smart key 102 shaft head 414. Visible is a bottom rotor 701, the shaft 702 of which serves as a support and pivot for top rotor 501. The top rotor 501 is not directly, fixedly connected to the bottom rotor 701, and rotation of the top rotor 501 would not necessarily create rotation of the bottom rotor 701 directly. Intermediate components, shown in subsequent figures, facilitate interconnection between top 501 and bottom 701 rotors when pill box 101 is unlocked by smart key 102.

Bottom rotor 701 is connected downward to a drive plate 703 that has a drive peg 704 which can engage with a mating surface 705 of a top pill carousel 706 to turn top pill carousel 706 forward. This pill carousel 706, and each pill carousel 709 below pill carousel 706, can have a drive peg 707 that in turn can mate with and drive the next carousel 709 below. In the initial position, drive plate 703 and its drive peg 704 are engaged with carousel 706 and can advance it. As it does so, pills from within each well in the carousel 706 can fall down an open shaft in the carousels 706, 709 and out an exit slot 708. Once the top carousel 706 is advanced a full rotation, its drive peg 704 picks up the next carousel down 709, and rotates that carousel 709 to dispense its pills within the corresponding wells. The pill box 101 can be designed with various numbers of carousels 709. The medications are sealed in the pill box 101 by a seal 710 between the bottom rotor 701 and the drive plate 703, and a separate cap or plug (not shown) to cover the exit slot 708.

Figure 8:
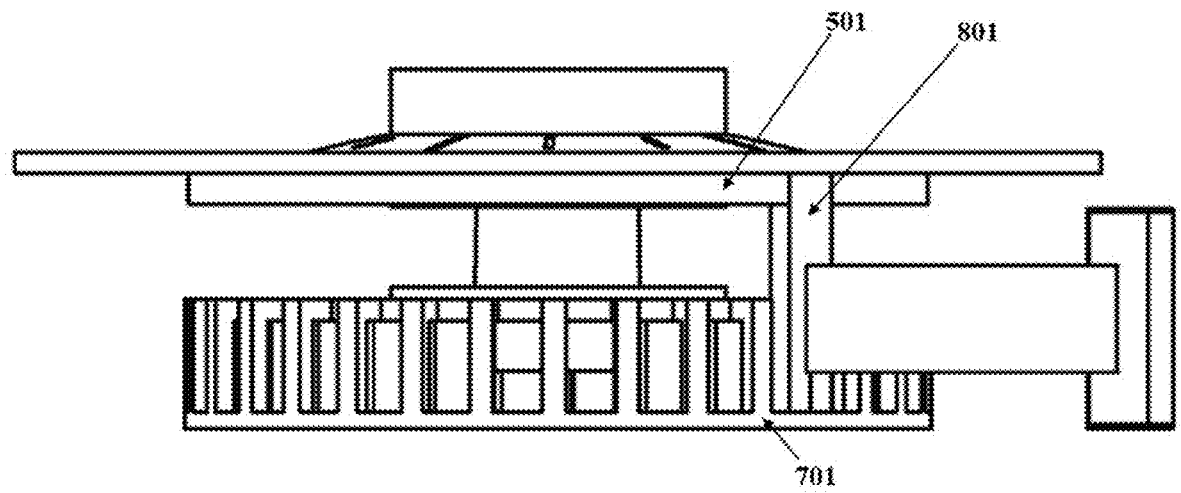
FIG. 8 is a figure showing certain components of an exemplary pill box.
Figure 9:
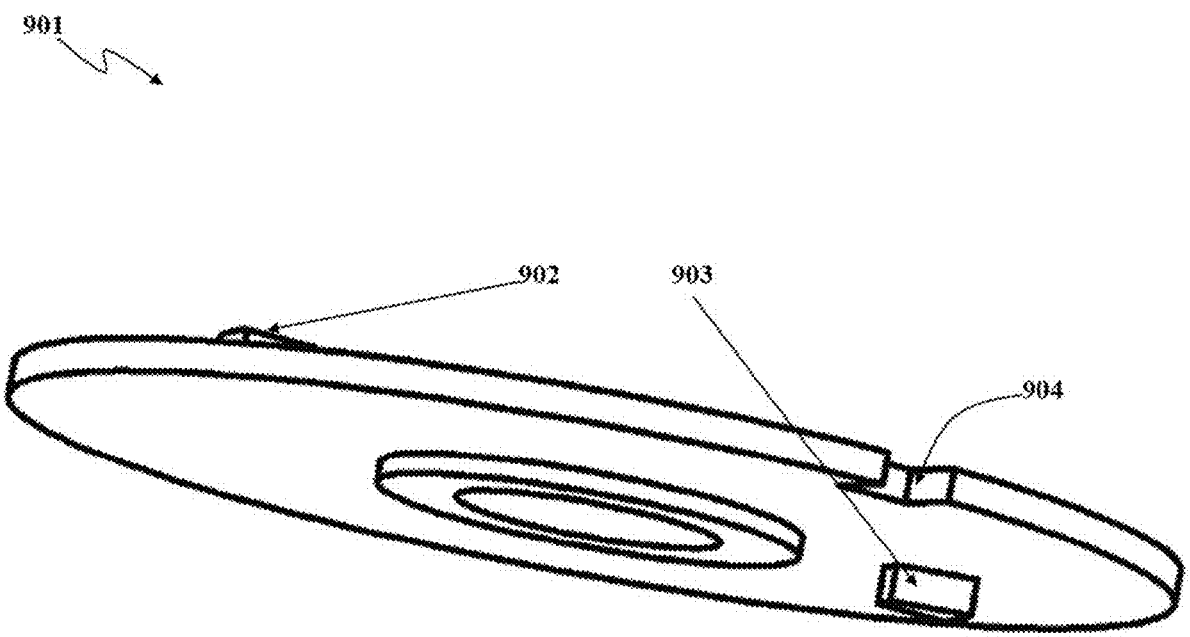
FIGS. 9 and 10 are perspective and top views of an embodiment rotor component of an embodiment pill box.
Figure 10:
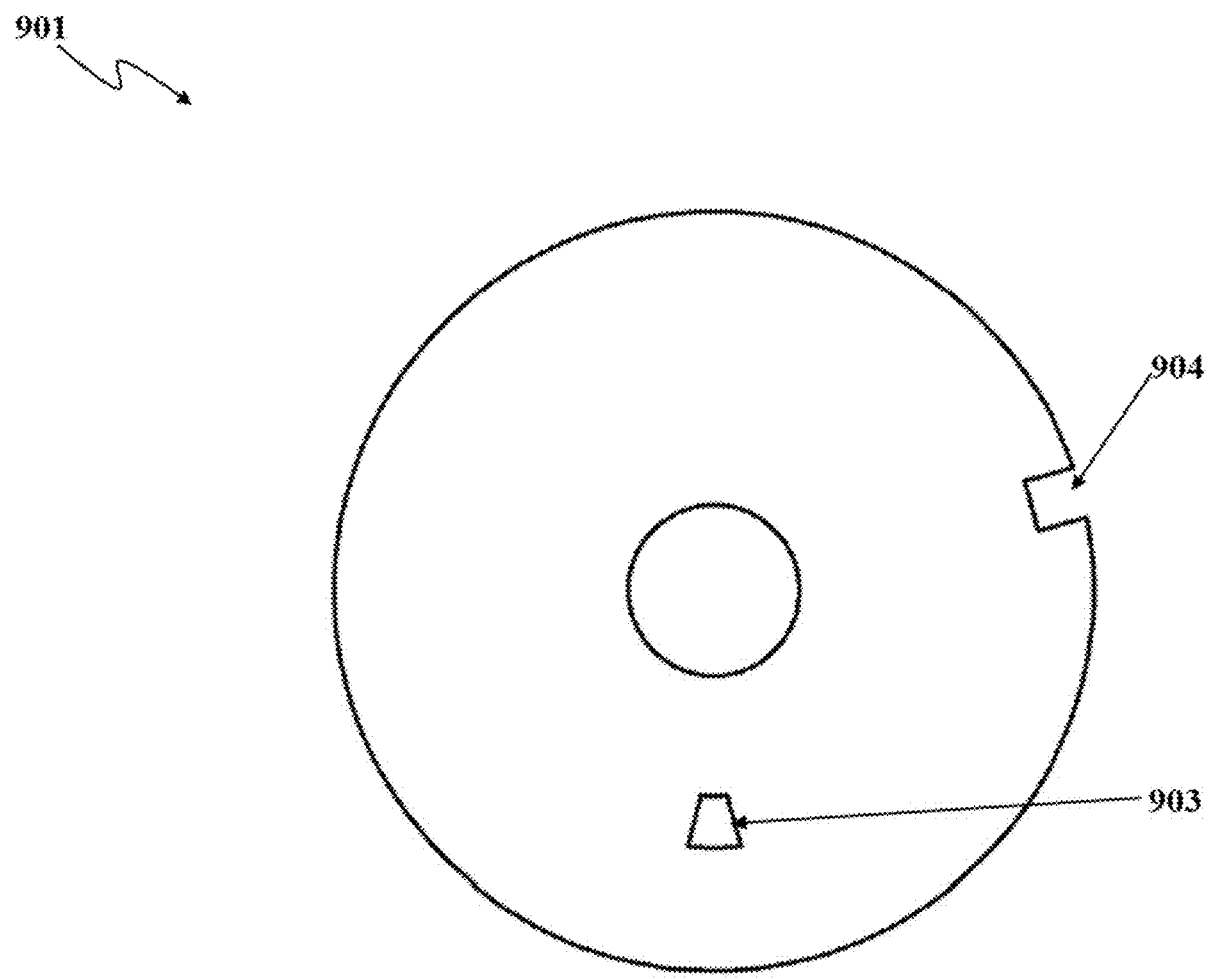
Figure 11:
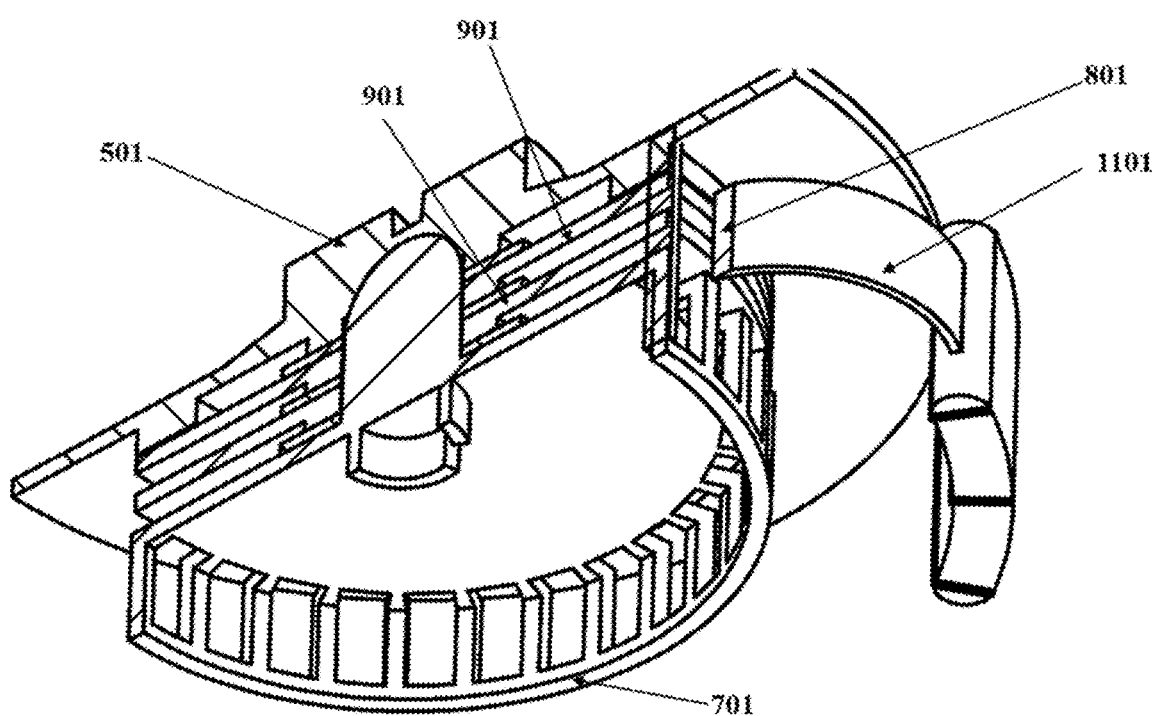
FIG. 11 is a perspective, cross-sectional view of rotors of an embodiment pill box.
Figure 12:
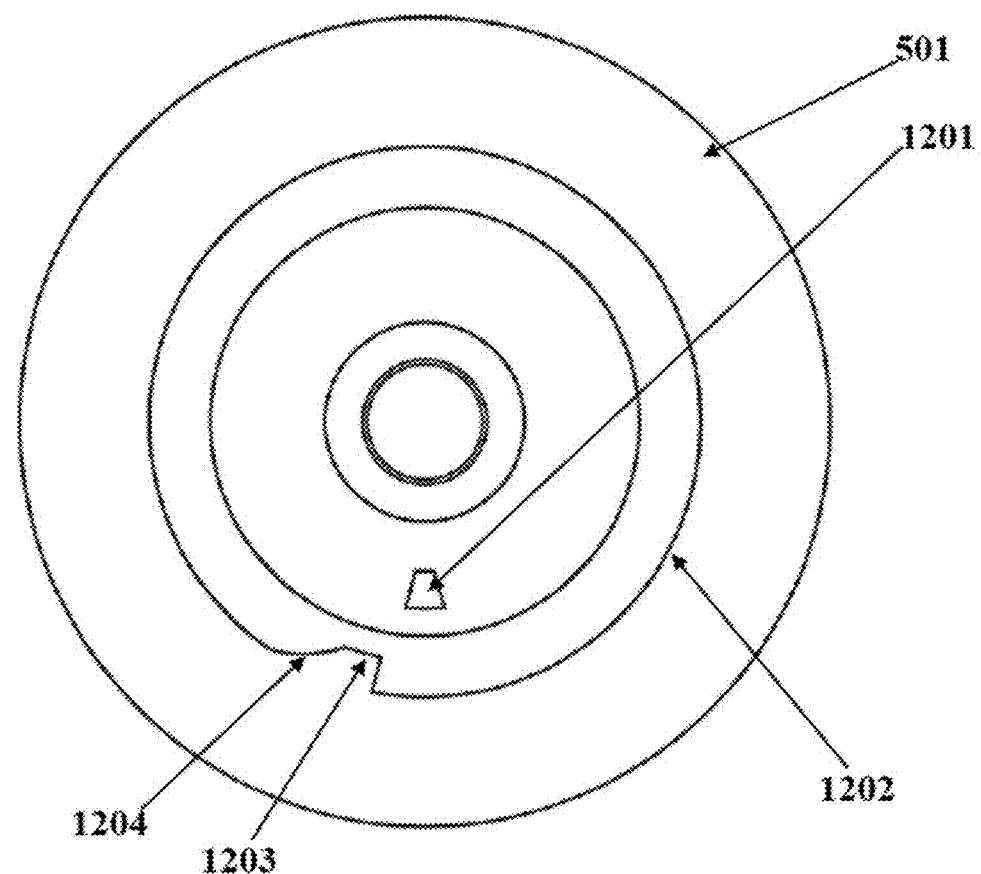
FIG. 12 is a bottom view of an embodiment top rotor.

The unlocking process occurs when rotation of top rotor 501 is temporarily connected to rotate bottom rotor 701. FIG. 8 shows a connecting arm 801 which can fit into slots on top rotor 501 and bottom rotor 701 to bind the rotation of one to the other. When pill box 101 is locked, this connecting arm 801 is fenced away from the slots by intermediate rotors 901 shown in FIGS. 9 and 10. These intermediate rotors 901 have drive pegs 902 and 903 on each side, to allow them to collide with and be pushed rotationally from the rotor 901 above, and have a slot 904 sized for the connecting arm 801. FIG. 11 shows a cross-section of the rotor stack, including the intermediate rotors 901. The unlock process described previously allows the top rotor 501 to sequentially push each rotor 901, 701 into a position. To unlock the device, each rotor 501, 701, 901 is moved so that the slots 904 align with the connecting arm 801, which has a spring 1101 that pushes the arm 801 radially inward and into the slots 904, 1203. FIG. 11 shows the state where the slots 904, 1203 of all rotors 501, 701, 901 have been aligned and the connecting arm 801 has sprung inward. Only then will rotational movement of the top rotor 501 be transmitted to the bottom rotor 701, and in turn through to the carousels 706, 709 holding pills below. FIG. 12 shows the underside of top rotor 501, which has a drive peg 1201 and a ridge 1202 that forces the connecting arm 801 out until the slot 1203 is aligned with arm 801. Once connecting arm 801 is in slot 1203, reversal of the top rotor 501 will force the ramp ridge 1204 to drive connecting arm 801 back out of the slot 1203, effectively creating again a locked state for pill box 101.

Figure 13:
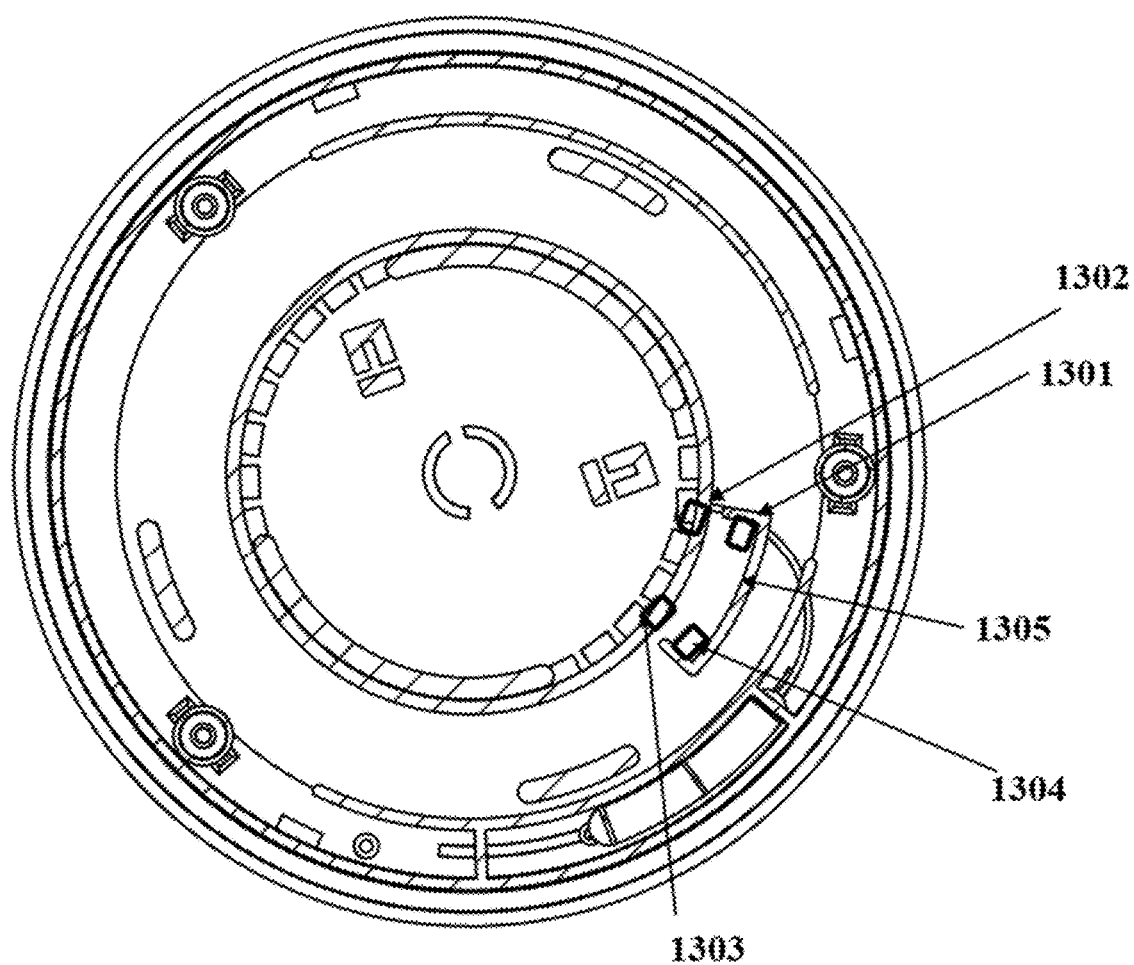
FIG. 13 is an interior view from a top perspective of a bottom rotor and possible positions of a connecting arm.

FIG. 13 shows from above the positions that connecting arm 801 goes through. Position one 1301 is the default locked position, defined by a corresponding barrier, where the connecting arm 801 is pushed out by misalignment of the rotor slots 904, 1203. Slot alignment allows spring 1101 to push connecting arm 801 into position two 1302. Advancement of the top rotor 501 then pushes arm 801 to position three 1303. Further advancement is constrained by another barrier 1305. Position four 1304 is achieved when top rotor 501 reverses, and spring 1101 action then pulls connecting arm 801 back to position one 1301. The sequence to unlock and advance the bottom rotor 701 can then be repeated by smart key 102. It will be appreciated that the circumferential distance from position one defined by the first barrier 1301 and position three defined by the second barrier 1305 can be used to set the number of units of pills that are dispensed, as this correspondingly determines the distance traveled by carousels 706, 709.

Figure 14:
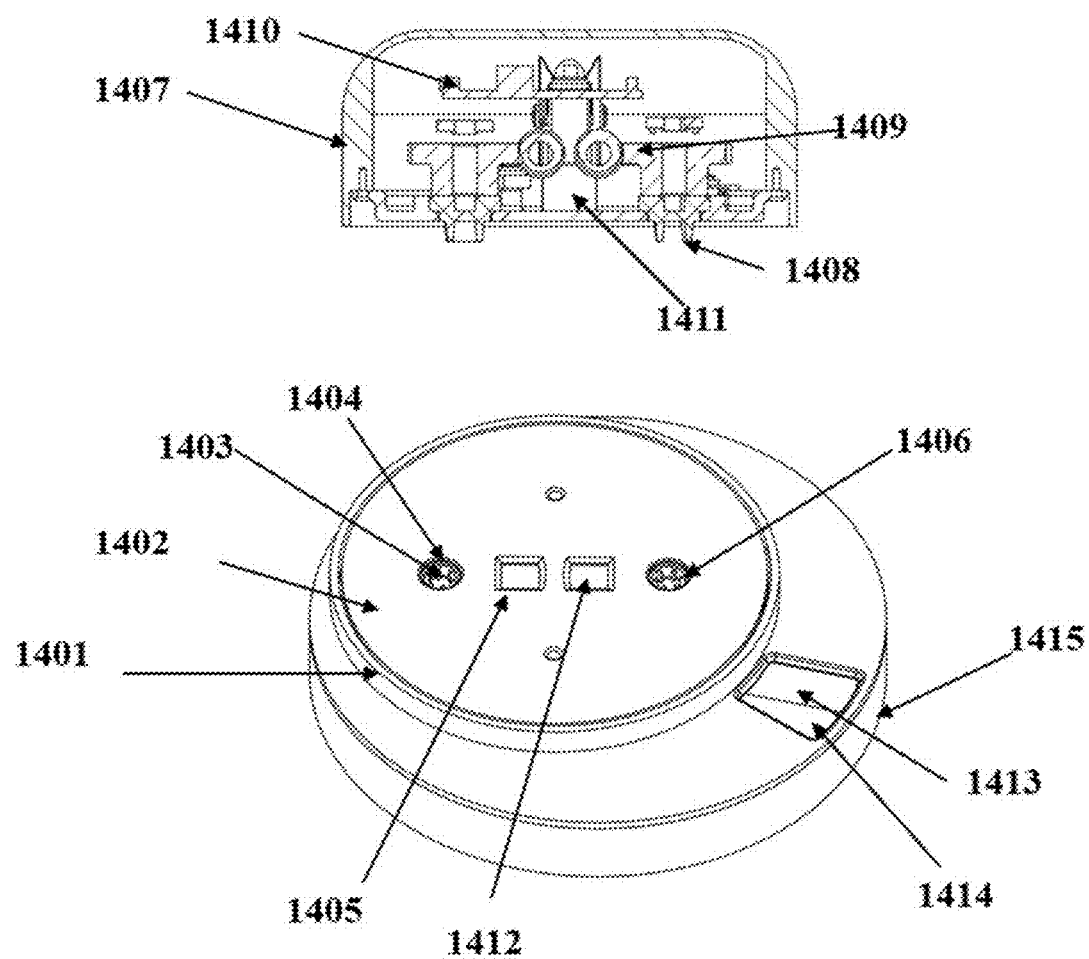
FIG. 14 is a perspective view of an alternative embodiment pill box.

An alternate embodiment of a pill box is shown in FIGS. 14 through 17. FIG. 14 shows a top housing 1401 containing a rotating top wheel 1402, which in turn houses two rotors 1403 that can be partially seen via drive holes 1404 in top wheel 1402, and via respective view windows 1405. Rotors 1403 each have a central well and inward facing sprockets 1406, such that a smart key configured with two motors and corresponding mating drive heads can turn each rotor 1403 independently and simultaneously. An exemplary smart key 1407 has two drive shafts 1408 that can be inserted through holes 1404 to engage with corresponding rotor sprockets 1406, and each drive shaft 1408 is connected to a respective motor 1409 and controlling electronics 1410 analogous to that of the smart key 102 shown in FIG. 4. Each view window 1405 allows smart key 1407 camera 1411 to watch a corresponding surface 1412 visible on the rotors 1403 through view windows 1405. These rotors 1403 are labeled with machine-readable indicia that are readable by smart key 1407 camera or cameras 1411 and underlying processing logic, and in the exemplary embodiment the labels are 2D barcodes printed using UV ink on the surfaces 1412 in a circular ring on the top of each rotor 1403. The smart key 1407 of this embodiment operates analogous to that of the previous embodiment described, in that a processor turns rotors 1403 to the appropriate positions to enable unlocking of the pill box and dispensing of medications from a carousel 1413 through an exit slot 1414. Carousel 1413 is sealed within top housing 1401 and a bottom housing 1415. The motors 1409 can be programmed to move rotors 1403 to a respective specific angular position. The smart key 1407 can confirm rotor 1403 position by reading the machine-readable indicia on top of the rotors 1403 via respective windows 1405.

Figure 15:
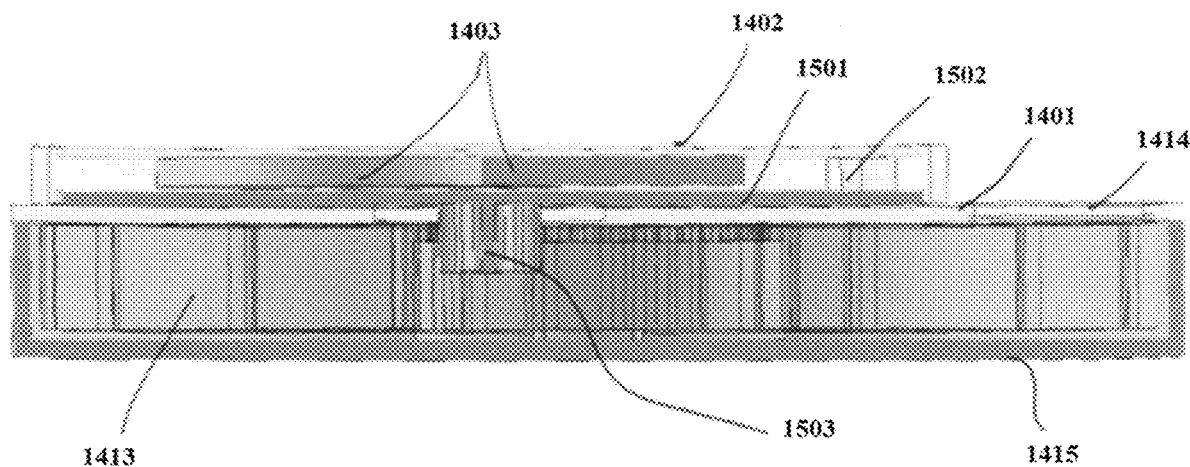
FIG. 15 is a side view of the components of the pill box shown in FIG. 14.

FIG. 15 shows a cross-section of the pill box shown in FIG. 14, showing that rotors 1403 are held by the top wheel 1402 and a bottom wheel 1501, which are connected together via screws or other connecting means 1502 to form a chassis for rotors 1403. Bottom wheel 1501 is molded to contain a spur gear structure 1503 facing downwards. Other components shown are top housing 1401, carousel 1413, bottom housing 1415, and exit hole 1414.

Figure 16:
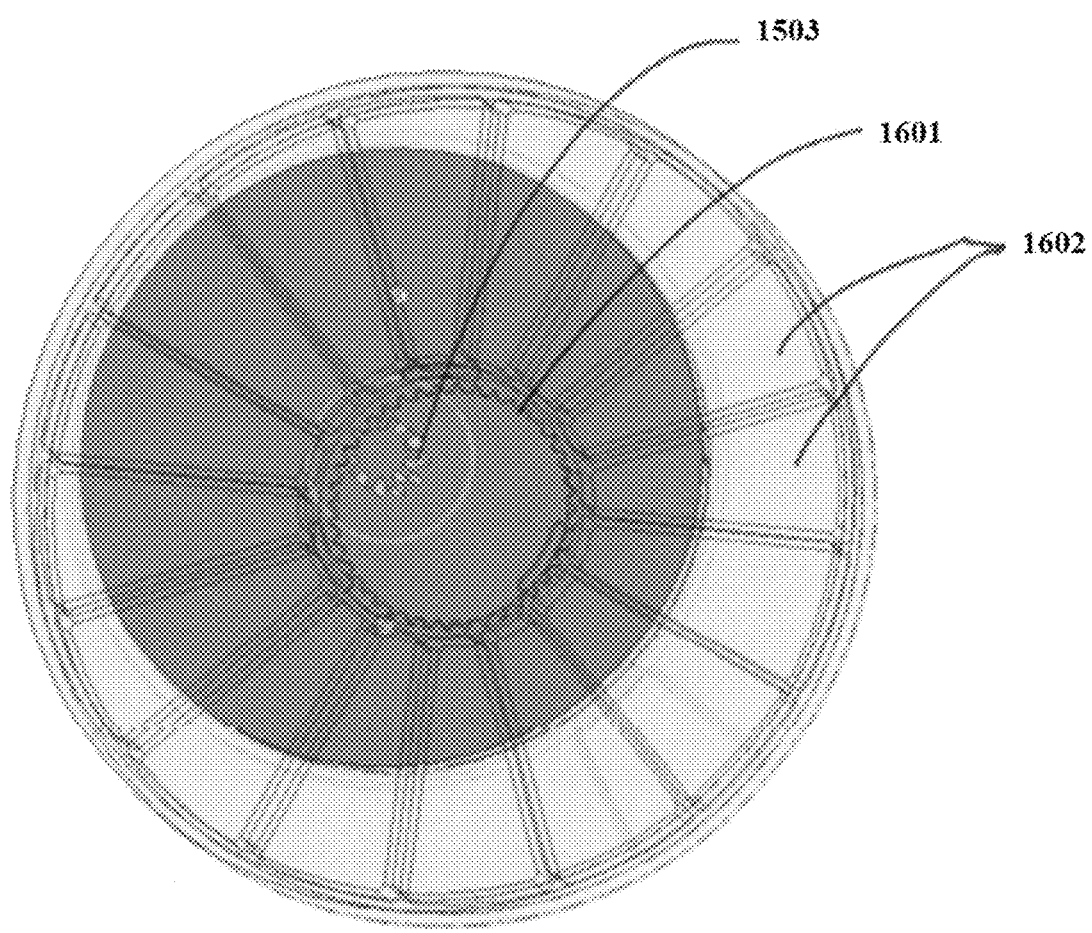
FIG. 16 is a top see-through view of components of the pill box shown in FIG. 14.

FIG. 16 shows a bottom view with bottom housing 1415 and carousel 1413 shown transparent. Spur gear structure 1503 interfaces with a planetary gear structure 1601 molded into carousel 1413, assuring that turning of the top/bottom wheels will turn carousel 1413, which in turn will enable access to medications in carousel 1413. Carousel 1413 has wells 1602 into which medication is placed. Once filled with medication, carousel 1413 is placed in bottom housing 1415. Top housing 1401 is placed over bottom housing 1415 and snap fit formations hold top and bottom together in a manner that does not permit for manual disassembly. The only means of removing pills is through exit hole 1414 in top housing 1401 which reveals one carousel well 1602 at a time. Carousel 1413 is geared into the top wheel 1402 via its attachment to the bottom wheel 1501, its spur gear 1503, and the carousel planetary gear 1601. Top wheel 1402 will not advance unless the rotors 1403 are positioned properly.

Figure 17:
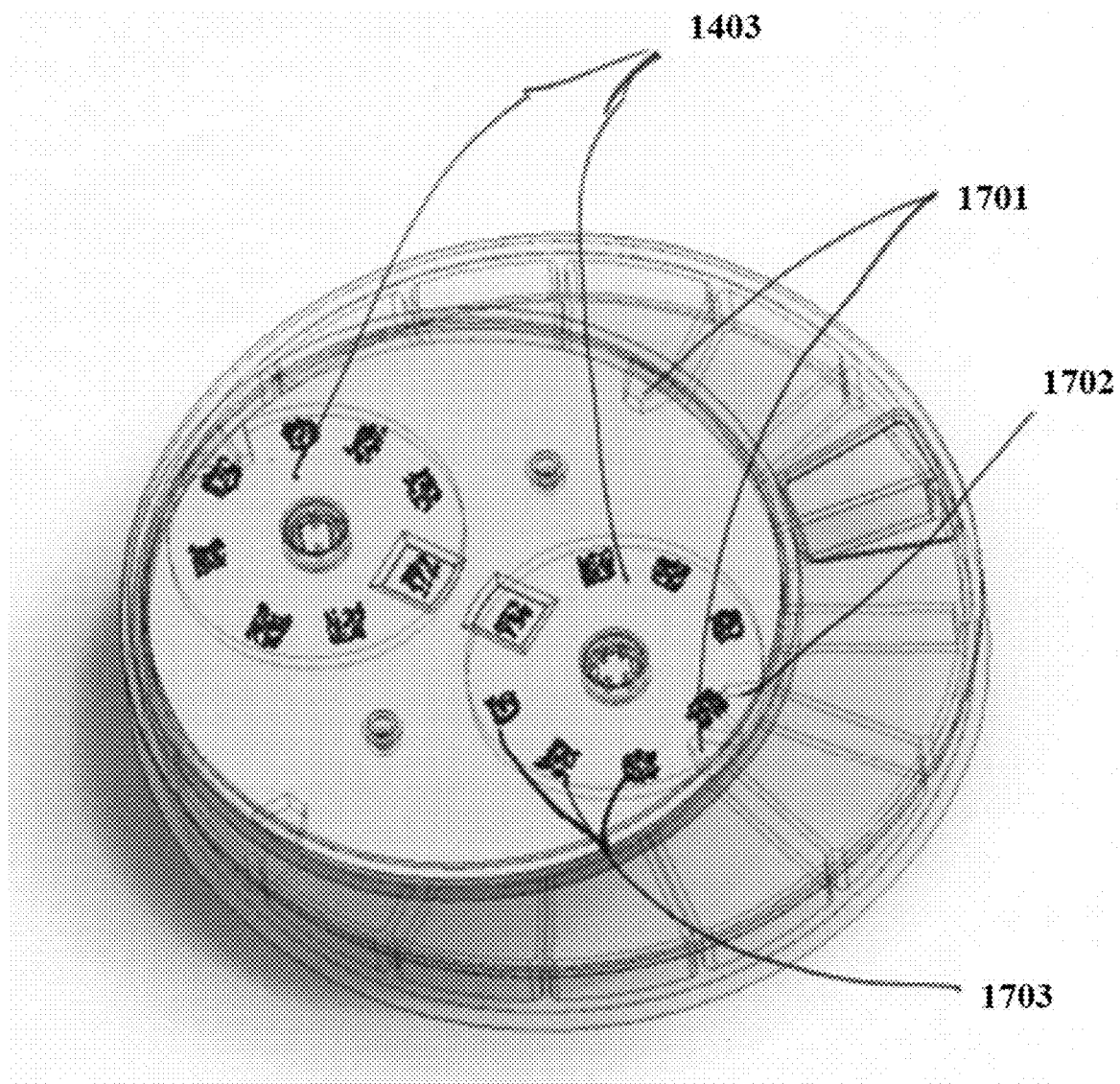
FIG. 17 is a perspective see-through view of the pill box shown in FIG. 14.
Figure 18:
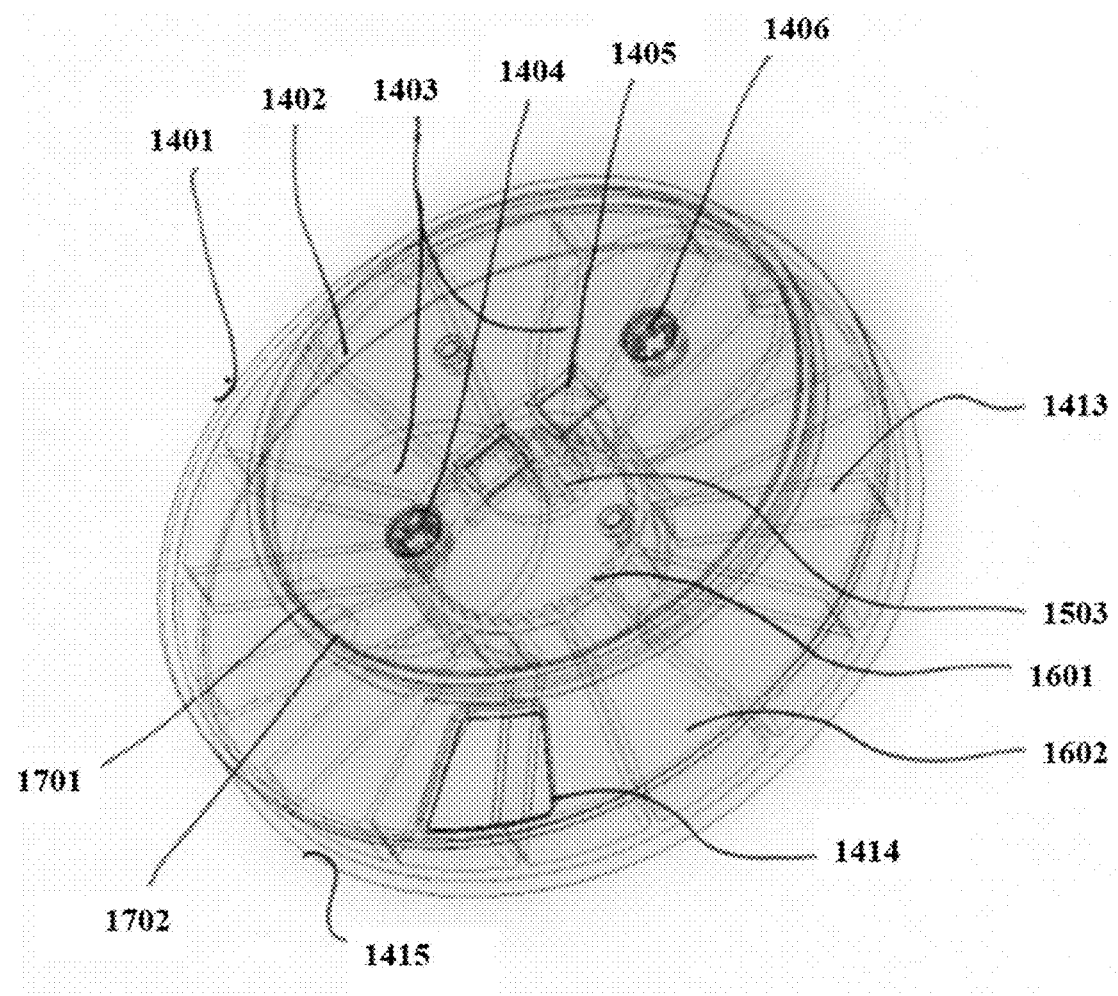
FIG. 18 is another perspective see-through view of the pill box shown in FIG. 14.

FIG. 17 is a top view with top housing 1401 and top wheel 1402 shown transparent. The rotation of the assembly formed by top/bottom wheels and rotors can be blocked by pegs 1701 that protrude from top housing 1401 to collide with rotors 1403. When rotors 1403 are set to a specific position by smart key 1407, voided space 1702 on the underside of each rotor 1403 is lined up with pegs 1701 and allows the entire subassembly to rotate past pegs 1701. When rotors 1403 are properly aligned, the user can twist the smart key 1407 to advance top wheel 1402 forward, for example, 90 degrees until being stopped by another set of pegs 1701, and this forward rotation also rotates forward carousel 1413 by one well 1602, as determined by gearing of sprocket 1503, allowing the next medication dose to advance underneath the hole 1414. The smart key 1407 can use machine-readable indicia 1703, such as barcodes, printed on the top surface 1412 of rotors 1403 and visible through windows 1405 to confirm proper alignment of rotors 1403. FIG. 18 provides another transparent view of the components of this exemplary pill box.

Figure 19:
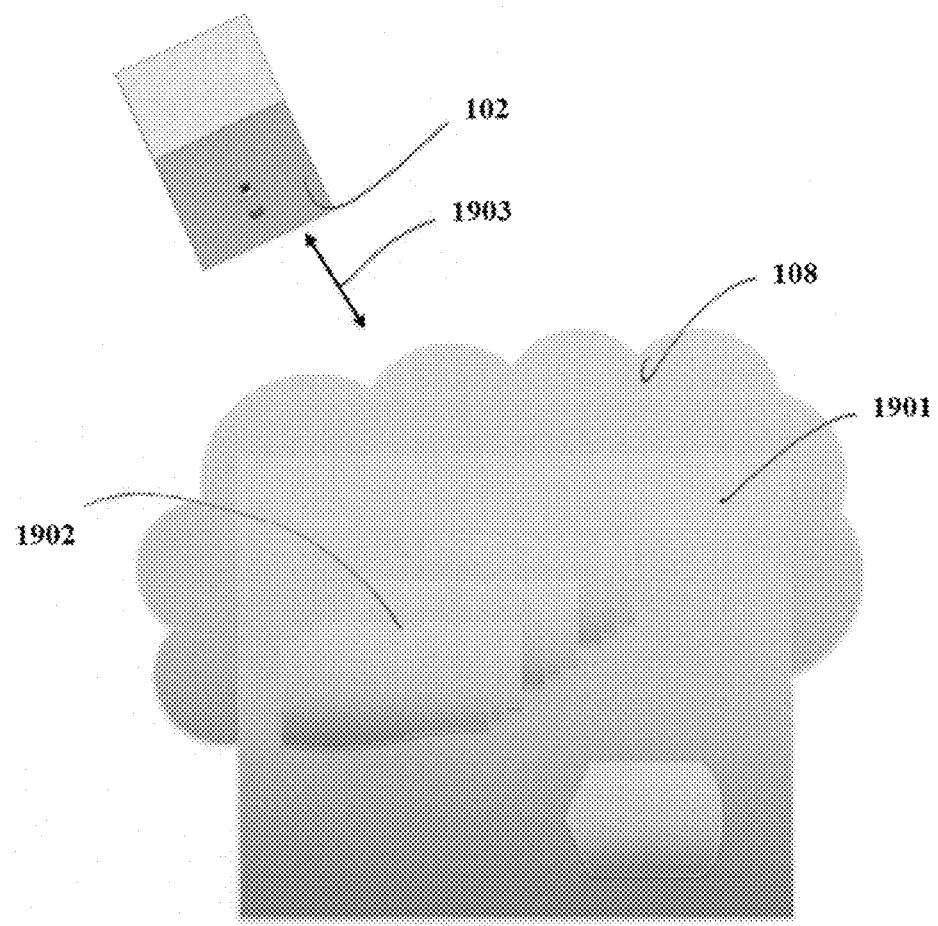
FIG. 19 shows components of a therapy management system that leverages embodiment smart key and pill box medication management technology in conjunction with psychological therapy.

FIG. 19 depicts a treatment system provided by the exemplary embodiments of the pill box containers and smart key. The exemplary treatment system integrates the medication access control and monitoring technology described herein with psychological therapy and support. The exemplary treatment approach is for pain management, but one of ordinary skill in the art could create similar programs for other treatment domains, such as ADHD, depression, etc.

A patient-accessible computing device 1901, e.g. a smartphone, tablet or computer, is designed to run an application 1902 that serves as a Mobile Electronic Diary for Treatment (MED-T). The patient computing device 1901 has a communication path 1903 with an embodiment smart key. The patient computing device 1901 can be the same master system 108 shown in FIG. 1, for example, and the application 1902 may be considered a component and extension of that system 108. The MED-T application 1902 enables users to track and report symptoms, emotions, and behaviors in real-time, facilitate easy access to interventional content in vivo, and manage prescribed medication regimens.

Treatment events depicted in reports can include scaled summary scores of outcomes, pain, functioning, side effects, length/quality of sleep, medication problems, and adherence. The patient's status can be used to determine their access to medications, enforced dynamically because the smart key can control access to medications. In turn, the smart key can provide accurate tracking of medication usage data that can be used to personalize the treatment approach. Together these capabilities work synergistically to motivate a patient towards proper behavior, and deter the patient from undesirable behavior.

FIGS. 20-29 illustrate yet another embodiment of a medicament dispensing system. The system includes a pill box 2001 that is provided to a patient in the form of a locked and sealed container and into which a pharmacist can deposit up to, for example, twenty doses of medication. The system further includes a smart key 2002, which is an electronic device that can be used by the patient to unlock pill box 2001 at the appropriate times to allow the patient access to a dose of medication. Each smart key 2002 can be used with multiple pill boxes 2001, allowing the patient to use a single smart key 2002 for all of their medication access.

Figure 21:
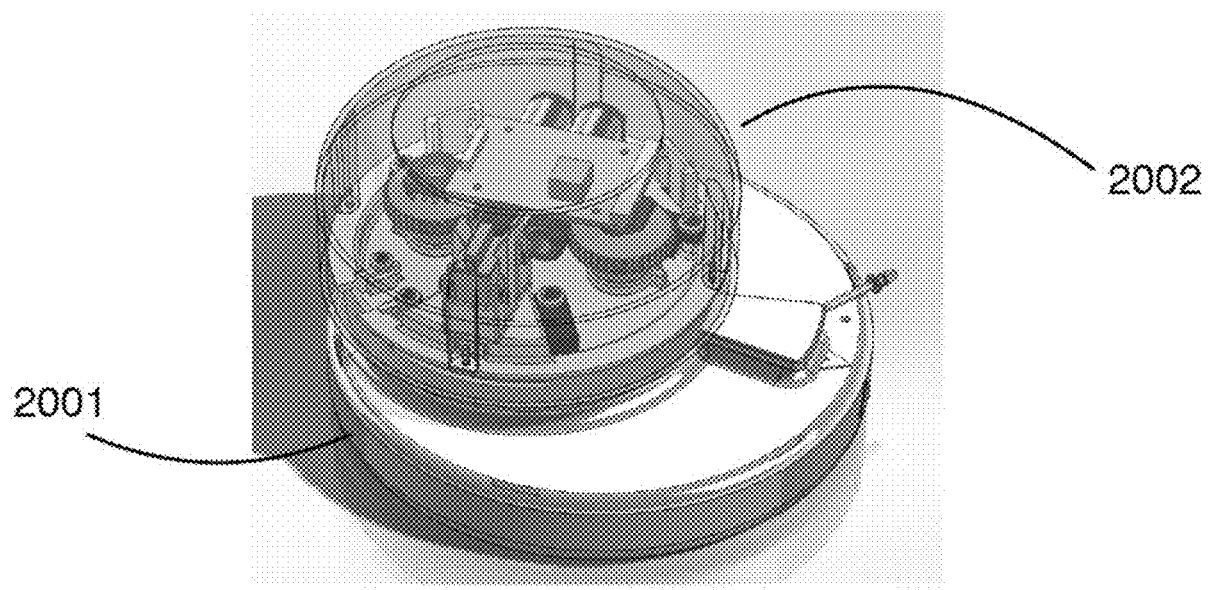
FIG. 21 shows the medicament dispensing system of FIG. 20 in a coupled state.

As illustrated in FIG. 21, to utilize the medicament dispensing system, the patient simply places smart key 2002 on pill box 2001. To obtain a dose of the medication contained within pill box 2001, the patient rotates smart key 2002 one-quarter turn, for example, which causes pill box 2001 access window 2211 to align with a new pill carousel space 2203. When no dose is required, smart key 2002 can indicate this in any suitable manner, such as with an LED indicator, a screen readout, a sound, etc.

Figure 22:
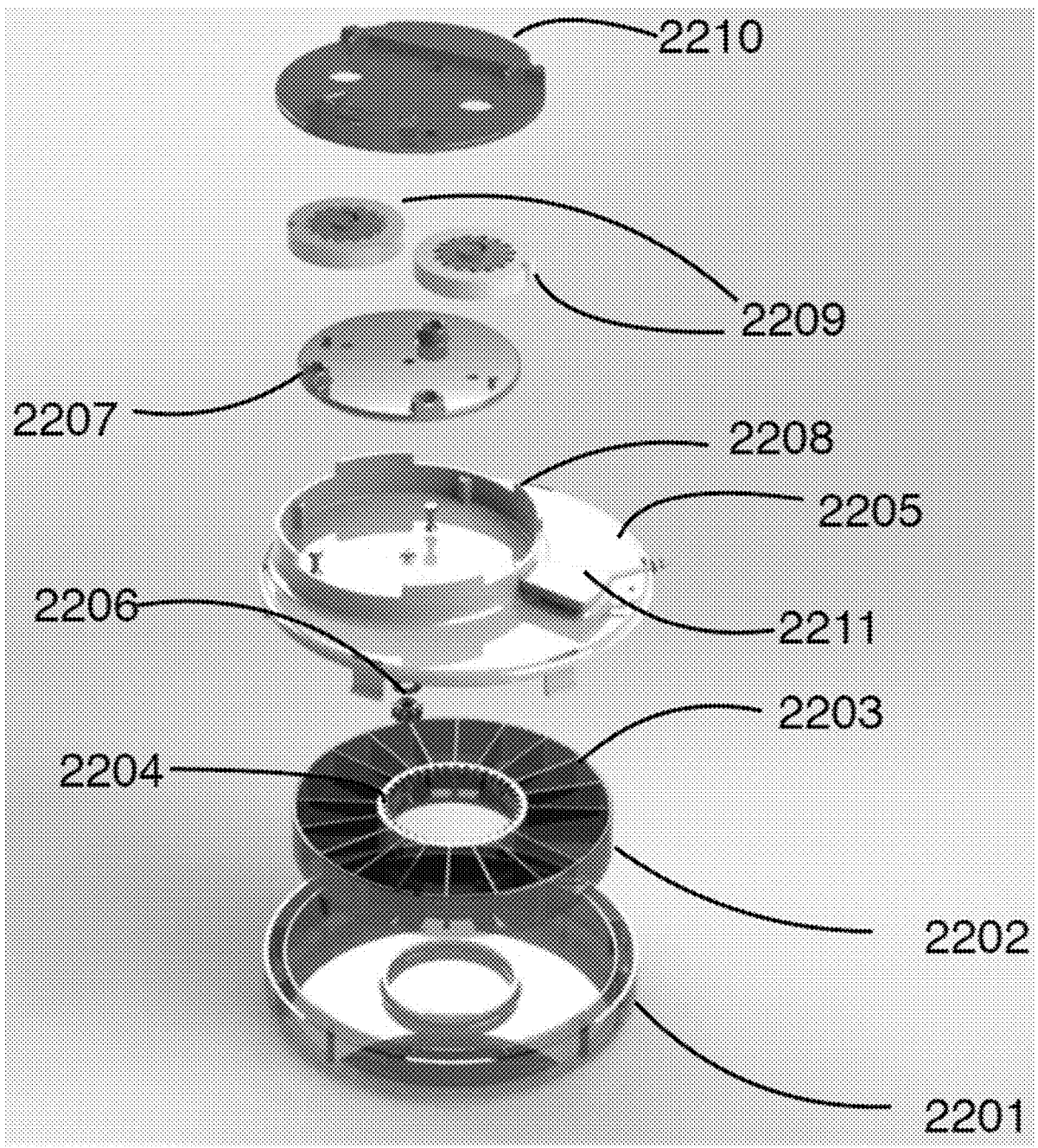
FIG. 22 is an exploded view of a pill box shown in FIG. 20.

As shown in FIG. 22, which provides an exploded view of the components of the exemplary pillbox 2001, the medication is stored in a rotating carousel 2202 inside a durable, sealed housing provided by a bottom cover 2201 and top cover 2205. Bottom cover 2201 and top cover 2205 can be provided in a disassembled state along with carousel 2203, and can include respective snap fittings such that when the covers 2201, 2205 are brought together, they mechanically engage with each other and cannot thereafter be separated, with the carousel 2202 then rotatably sandwiched between the covers 2202, 2205.

A wheel assembly comprising a top wheel 2210 and bottom wheel 2207 on top housing 2205 interfaces with smart key 2002 above and carousel 2202 below such that when smart key 2002 unlocks rotors 2209 in the wheel assembly and is rotated, for example, 90 degrees, carousel 2202 below advances one dosage slot 2203. Medication doses may be accessed through an opening under door 2211 on top housing 2205, which can be sealed against moisture with an elastomeric (e.g., rubberized) door.

Pill box 2001 is used to lock pills or other types of medication inside top housing 2205 and bottom housing 2201 unless smart key 2002 unlocks pill box 2001. Preferably, pill box 2001 allows access to only a single dose of medication at a time, for example, by allowing access to only a single dosage slot 2203 at a time. Pill box 2001 also preferably seals the pills against moisture and is designed so at to be easily filled and assembled by a pharmacist.

Figure 23:
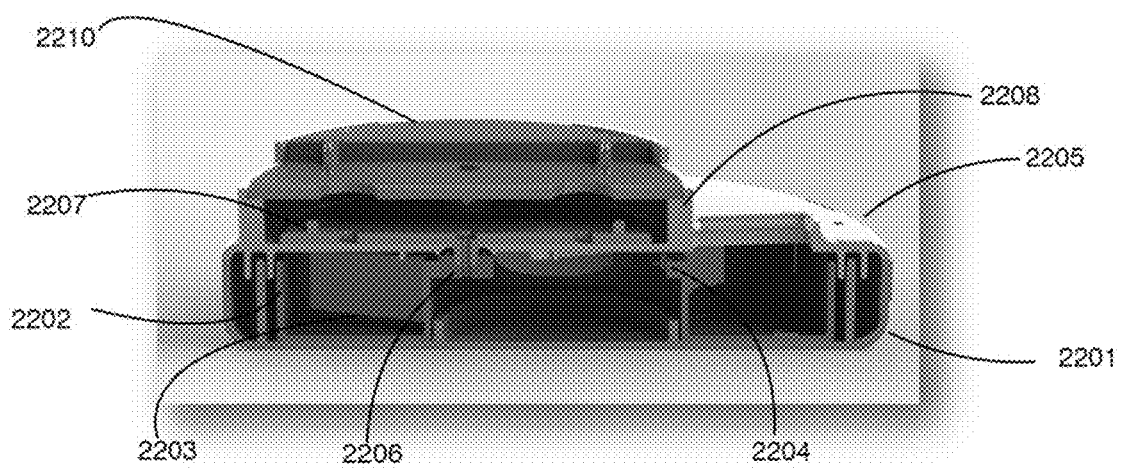
FIG. 23 is a cross-sectional view of the pill box shown in FIG. 20.
Figure 24:
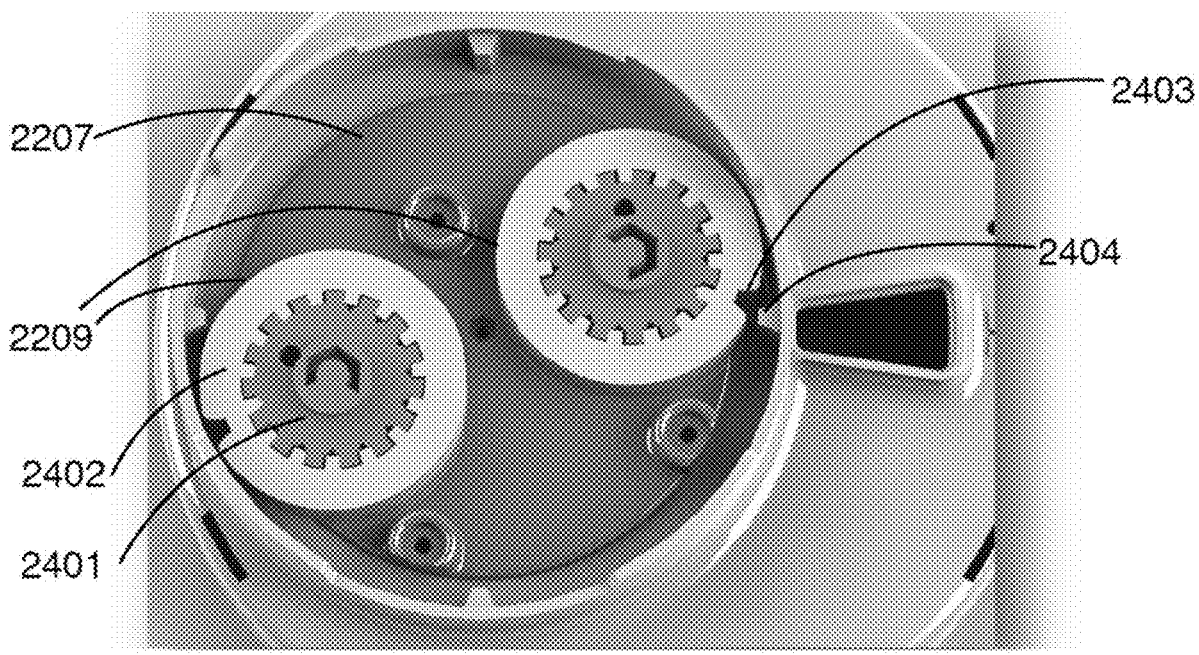
FIG. 24 is an internal view of the pill box shown in FIG. 20.

As illustrated in FIGS. 22-24, pill box 2001 includes a bottom cover 2201 that houses carousel 2202 and provides a base of the pill box assembly 2001. Carousel 2202 nests inside bottom cover 2201 and has, for example, twenty individual slots 2203 for storing a single dosage of medication. Carousel 2201 has a hole in the center with an internal gear ring 2204 around the periphery of the hole to rotate carousel 2201.

A top cover 2205 seals against bottom cover 2201 and covers carousel 2202. A door 2211 in top cover 2205 is preferably the same size as a single carousel slot 2203, and aligns with one slot 2203 at a time. A spur gear 2206 is mounted inside top cover 2205 and engages internal gear ring 2204 of carousel 2202. Spur gear 2206 is mounted to a post on a bottom axis of wheel 2207, with the post passing through top cover 2205 so that spur gear 2206 rotates whenever bottom wheel 2207 is rotated.

Bottom wheel 2207 rests on top of top cover 2205 and is surrounded by, and rotates within, a thin cylindrical wall 2208 protruding upward from top cover 2205. Two rotors 2209 are rotatably mounted onto bottom wheel 2207. As shown in FIG. 24, each rotor 2209 includes a core 2401 and an outer ring 2402, which as an assembly are rotatably mounted on to bottom wheel 2207. The rotor outer rings 2402 each have a single involute notch 2403 along an exterior edge which interlocks with corresponding engaging teeth 2404 on the interior of cylindrical wall 2208 of top cover 2205 when properly aligned. However, when notches 2403 are not aligned with engaging teeth 2404, rotors 2209 prevent bottom wheel 2207 from rotating inside top cover 2205, and thus prevent the rotation of spur gear 2206 and any corresponding interaction with carousel 2202.

Figure 25:
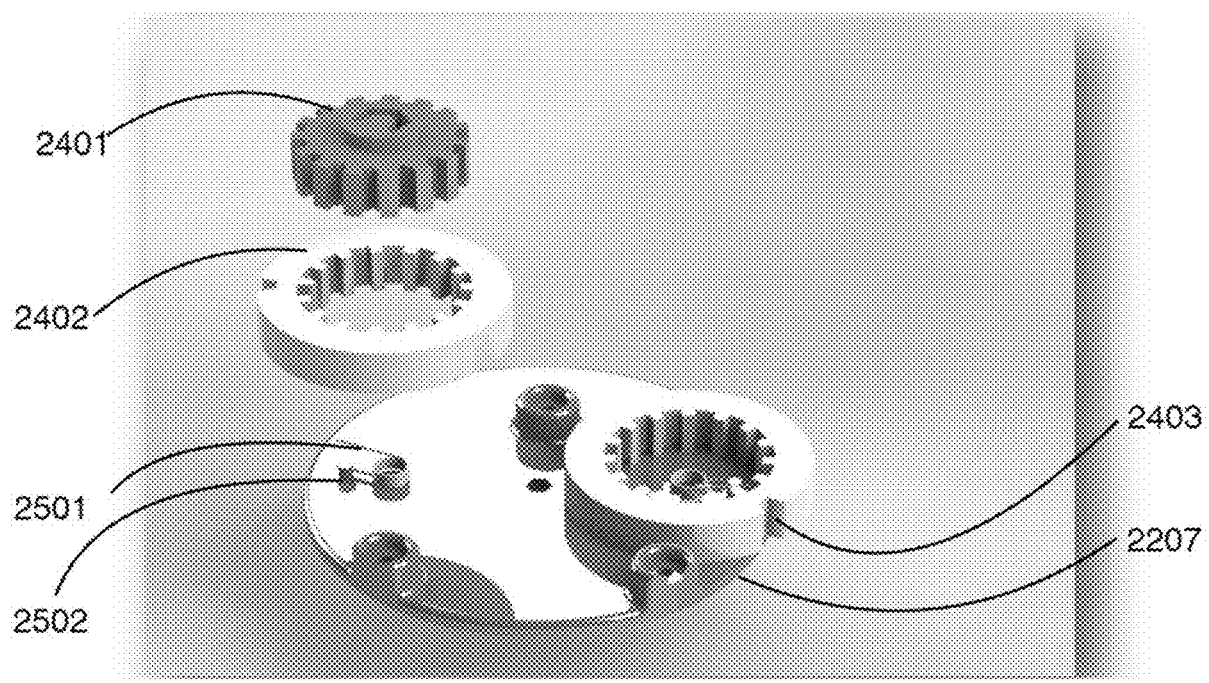
FIG. 25 is a detailed exploded view of the pill box shown in FIG. 20.

As shown in FIG. 25, underneath each rotor 2209 is a spring 2501 that rotates rotor core 2401 and outer ring 2402 back to a home or resting position after use. A respective post on rotor ring 2402 and a post 2502 on bottom wheel 2207 are in contact with spring 2501 to ensure that the resting position of every rotor core 2401 is always the same. The unlocking process requires rotating the rotor 2209 from this home position to a position in which the notch 2403 and engaging teeth 2404 can engage. The outer ring 2402 can be placed in various positions relative to the rotor core 2401, by way of any suitable interlocking structure, such as teeth, and thus different unlocking processes can be provided that require different amounts of rotation for each position of the outer core 2401. For example, the outer ring 2402 can be placed on the inner core 2401 such that the notch is near post 2502 that creates a resting position for the inner core 2401, or the outer ring 2402 can be placed on the inner core 2401 such that the notch is rotationally distant from post 2502.

Figure 26:
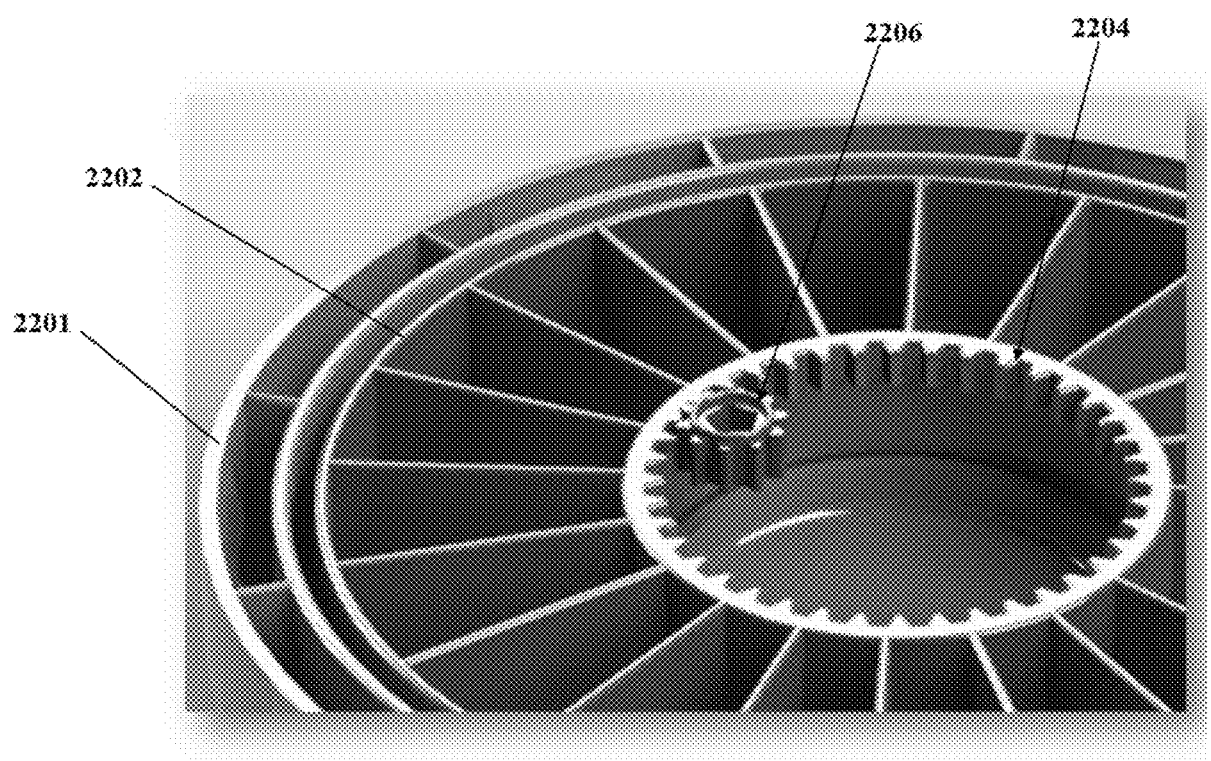
FIG. 26 is a detailed internal view of the pill box shown in FIG. 20.

In order to prevent improper medication access, carousel 2202 preferably exposes only one new dose at a time. As shown in FIG. 26, carousel 2202 rotates within bottom cover 2201, and is rotated by interaction with spur gear 2206 attached to bottom wheel assembly 2207. To prevent the free rotation of carousel 2202, bottom wheel assembly 2207 fits into top cover 2205 and contains the two rotors 2209 which stop against engaging teeth 2404 inside cylindrical wall 2208 of top cover 2205. The teeth 2404 in top cover wall 2208 are in, for example, four equal-distant positions around the inside perimeter of wall 2208, so that bottom wheel 2207 stops every ninety degrees of rotation. Carousel 2202 inner gear ring 2204 has, for example, fifty teeth while spur gear 2206 has ten teeth, so that each complete turn of spur gear 2206 corresponds to carousel 2202 rotating one-fifth of a complete turn, while a one-quarter turn of spur gear 2206 rotates carousel 2202 by one-twentieth of a complete turn. It will be appreciated that with twenty dosage slots in carousel 2202, this means that a one-quarter turn of the wheel assembly, and the attached spur gear, results in the advancement of the carousel by one single medication slot 2203. It will be further appreciated that the relative gearing between spur gear 2206 and inner gear ring 2204 can be changed to accommodate different numbers of slots 2203, to change the number of slots 2203 that are dispensed with each dispensing cycle, or both.

On top of the two rotors 2209 is a top wheel 2210, which covers the rotor mechanism 2207, 2209 from view and from tampering, as well as providing a surface for interacting with smart key 2002 to lock into place on pill box 2001 and rotate the wheel assembly 2210, 2207 relative to top cover 2205. Top wheel 2210 includes two openings respectively corresponding to rotors 2209 to permit rotation of rotors 2209 via engagement with axles of cores 2401. If a rotor 2209 is rotated so that the next engaging tooth 2404 will fit into the rotor notch 2403 instead of creating interference, the rotor 2209 is then in the unlocked position, and the rotor 2209 will catch the tooth 2404 and rotate past it without restriction. Both rotors 2209 must be in an unlocked position for the top and bottom wheels 2207, 2210 to rotate past a pair of engaging teeth 2404 (which allows carousel 2202 to rotate to a new dose slot 2203). Smart key 2002 interlocks with mating components of pill box 2001 and, with programmatic awareness of the position of each outer ring 2402 in pill box 2001, mechanically rotates the rotors 2209 the correct amount to facilitate unlocking, i.e., advancement of the top and bottom wheels 2210, 2207. Twisting of the entire smart key 2002 by 90 degrees then rotates carousel 2202 forward one slot 2203 and allows access to a new dose of medication.

The rotor outer rings 2402 can be placed in various positions on the inner cores 2401. Thus, once top wheel 2210 is in place and prevents visible inspection of rotor 2209 positions, previous knowledge of the exact positioning of the rotor 2209 outer rings 2402 is necessary to facilitate rapid alignment of rotors 2209 and thus advancement of the pill-carrying carousel 2202. Smart key 2002 preferably includes mechanisms and can be programmed with control logic to place rotors 2209 into the unlocked position, such that only a patient in possession of a valid and activated smart key 2002 will have facilitated access to pills in pill box 2001.

Door 2211 covers the access hole on top cover 2205 and seals this opening. O-rings, gaskets, seals or the like can be provided for assembly and sealing of the components, as known in the art.

Figure 27:
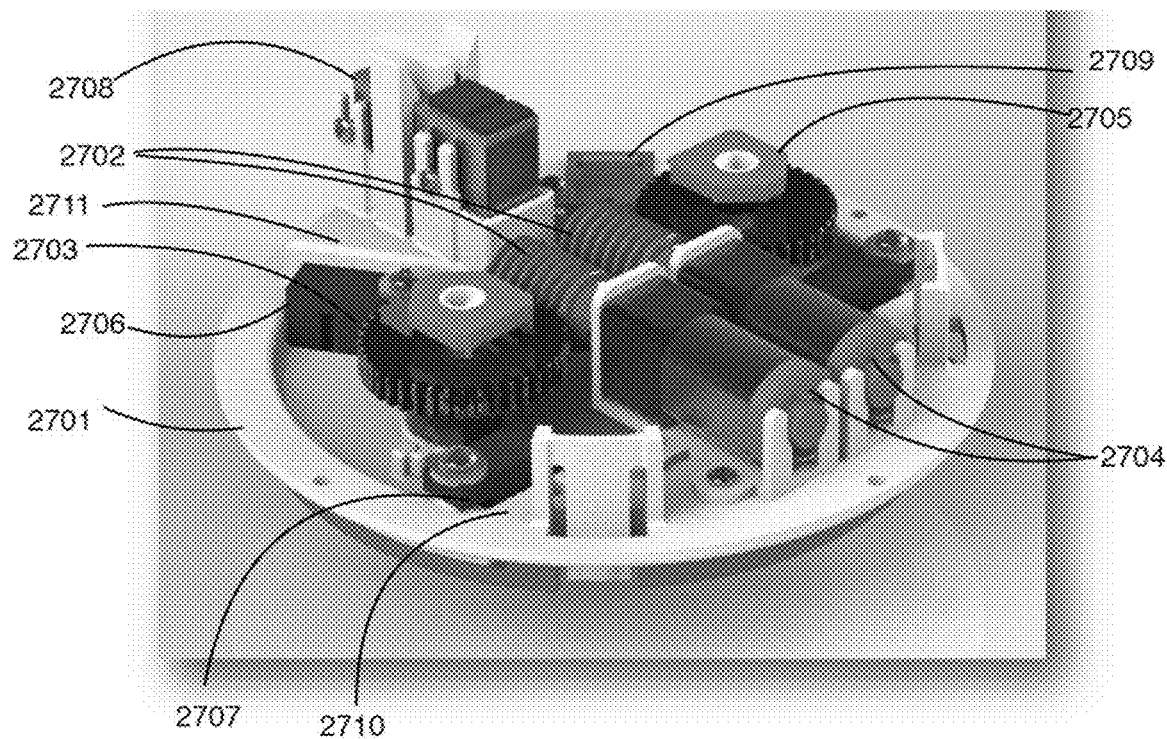
FIG. 27 is an internal view of a smart key shown in FIG. 20.

As shown in FIG. 27, smart key 2002 include a chassis 2701 that provides a base for smart key 2002 and that also mates to top wheel 2210 of pill box 2001. Rotor drivers have a first end extending from underneath chassis 2701 with a raised mating pattern corresponding to a recessed pattern present on the pill box 2001 rotor cores 2401, interlocking and ensuring simultaneous rotation between the mating components. Worm gears 2702 and worm wheels 2703 transmit power to the rotors 2209 via the rotor drivers. Micro-gearmotors 2704, which may include stepper motors, are mounted to chassis 2701 on, for example, limited-range swing arm mounts, and power the gears 2702, 2703 for unlocking pill box 2001. Preferably, two potentiometers 2705 on opposite, second ends of the rotor drivers provide feedback about the position of the rotors 2209. In FIG. 27 potentiometers 2705 are shown floating, however in preferred embodiments they are mounted to a microcontroller, circuit board or the like.

A pair of fixed-distance optic sensors 2706 on, for example, a daughterboard can be mounted to the edge of chassis 2701 to provide rotational position feedback to the smart key 2002 computing system, allowing smart key 2002 to determine the rotational distance of the rotors 2209 from the teeth 2404 of the wall 2208, such as by monitoring changes in height of wall 2208. It will be appreciated, however, that any suitable rotational position detection system can be used for sensors 2706, including Hall-effect sensors, micro-switches, rotary encoders and the like. Additional slot optic sensors 2707 can also be provided to provide feedback about whether the smart key 2002 is in position on pill box 2001, one positioned, for example, on the side of the chassis 2701 near the wedge shape 2711 and two on the flat edge of the semi-circle 2710. In this embodiment, a reader for machine readable-indicia 2003 in the form of a barcode scanner 2708 and related lens are mounted on top of chassis 2701 wedge 2711, and read a barcode from top wheel 2210 of pill box 2001.

Smart key 2002 further includes a computing system 2709, which can include a microprocessor, data storage (including program code), a clock to track the date and time, and networking interface components, as well as local interfaces with the barcode reading mechanism 2708, sensors 2706, 2707, and the two motors 2704 to control rotation of the pill box 2001 rotors 2209 when appropriate. The program code is executable by the microprocessor to provide the overall desired functionality of smart key 2002, as known in the art. The smart key 2002 barcode reader 2708 scans the pill box 2001 to ascertain identification of that particular pill box 2001. However, it will be appreciated that any other suitable method and system may be employed to identify the pill box 2001 to the smart key 2002. Once smart key 2002 has knowledge of the identity of pill box 2001, computing system 2709 accesses a datastore (either locally or networked) to obtain or compute data about the unlock position of pill box 2001 rotor set 2209. Once determined, computing system 2709 of smart key 2002 can also access other data about the patient, treatment pill box 2001 or both to determine whether to unlock pill box 2001 for the patient to access a dose of medication. If access is authorized, a smart key 2002 attached to a pill box 2001 as shown in FIG. 21 can then position the pill box 2001 rotors 2209 to facilitate unlocking of the pill box 2001. Then, with a quarter turn of smart key 2002, the new dose is ready to be accessed, and smart key 2002 shuts down. Smart key 2002 may record in its data store information about the delivered dosage, such as date, time, amount, e.g., number of carousel spaces 2203 dispensed, an identification of the pill box 2001, such as read from the machine-readable indicia 2003, or any other suitable information in response to delivering a dose of medication. This information can also be transmitted to a remote computing device by way of the networking interface components.

Figure 20:
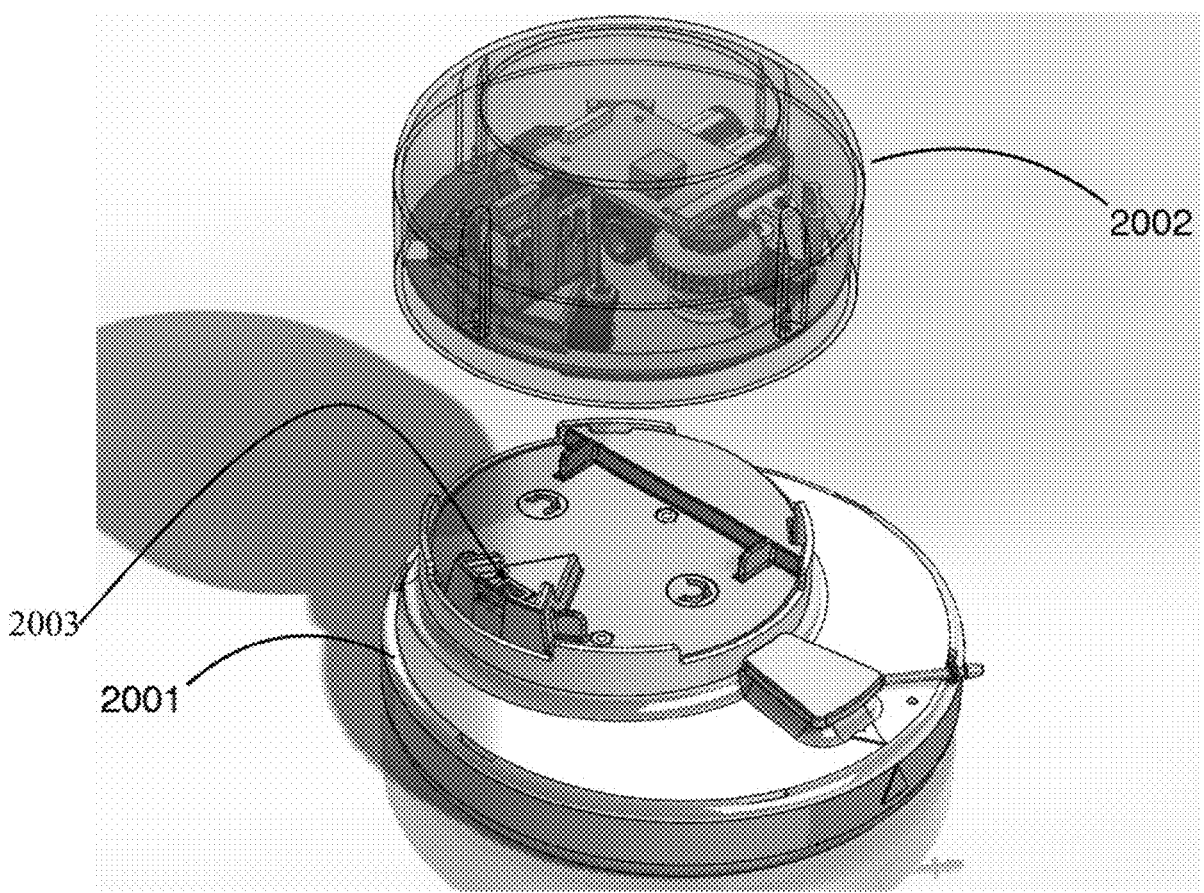
FIG. 20 shows an alternate embodiment of a medicament dispensing system.

A cover, as shown in FIG. 20, provides interior mounting for a PCB onto which are mounted the computing system 2709, indicator lights or a screen, and any other electronic components, as well as covering the smart key 2002 components and providing a comfortable surface for gripping and turning.

Figure 28:
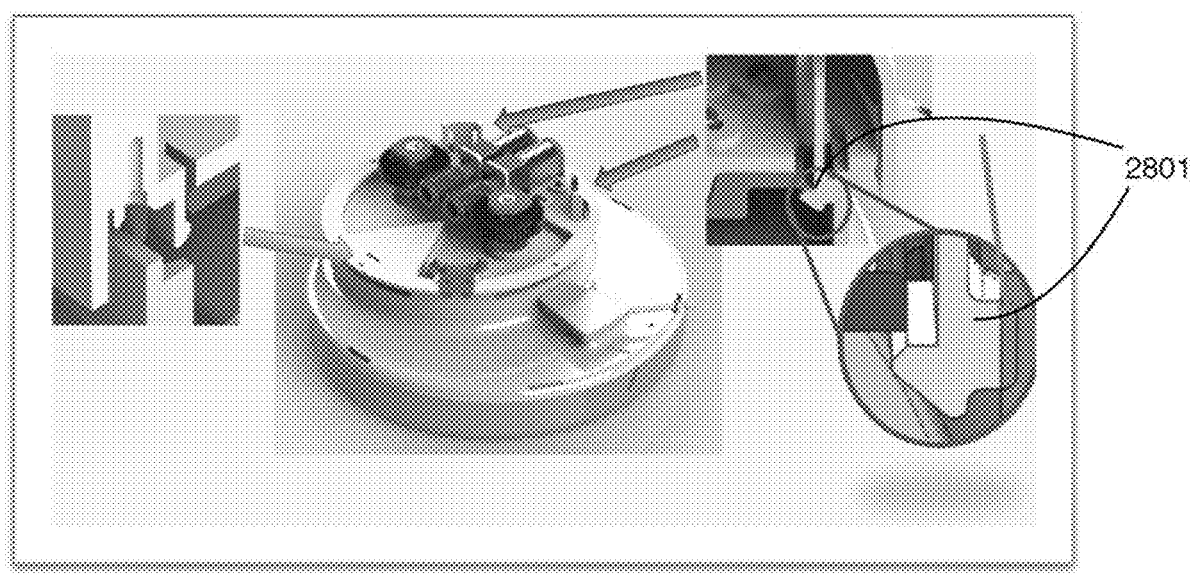
FIG. 28 illustrates coupling of the smart key and pill box shown in FIG. 20.
Figure 29:
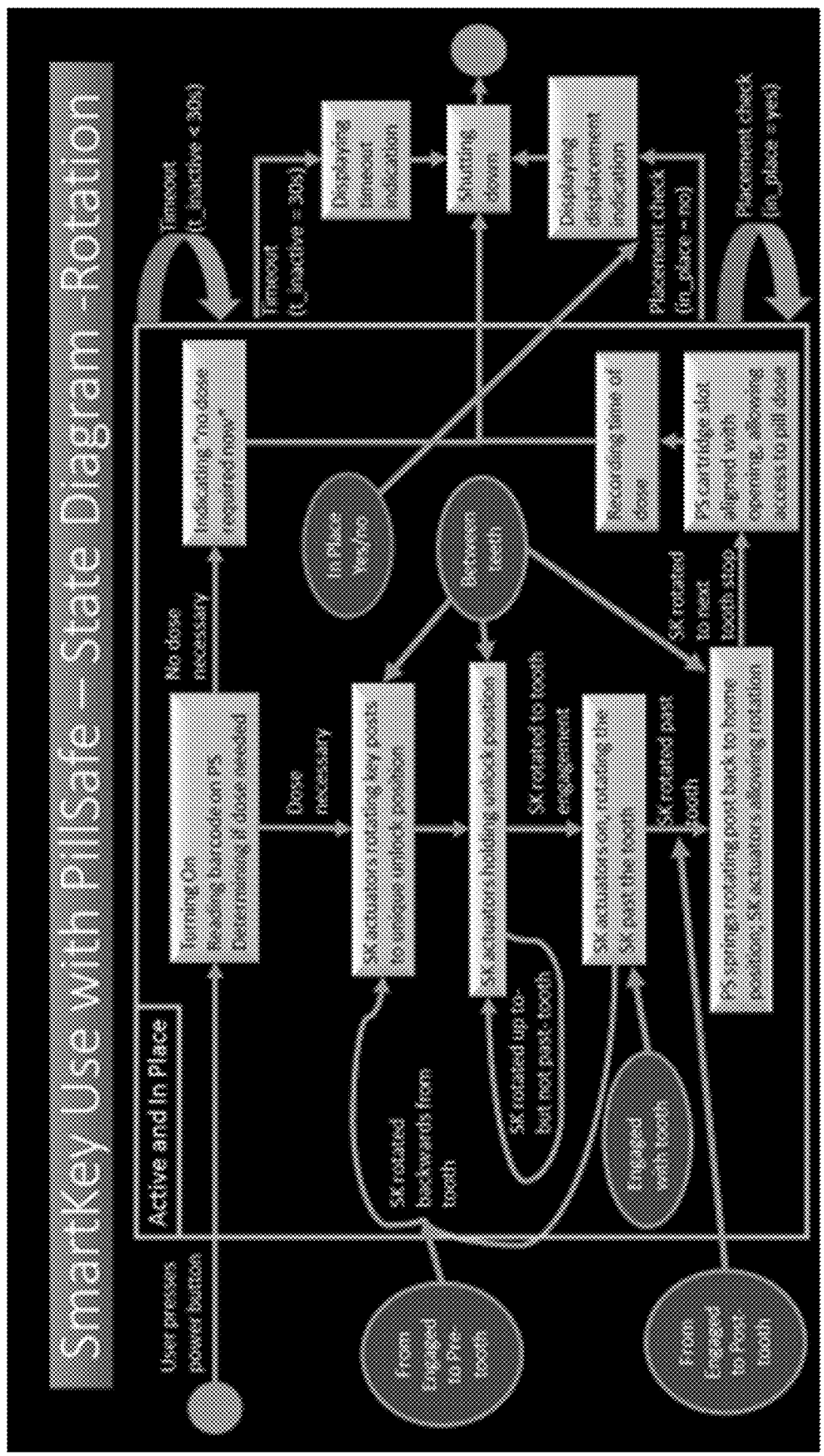
FIG. 29 is a flow chart illustrating use of the system depicted in FIG. 20.

Chassis 2701 of smart key 2002 snaps onto pill box 2001 as shown in FIG. 28. FIG. 29 shows a state diagram describing the various states of operation for smart key 2002. Operating smart key 2002 can include the following basic steps (if, for example, a dose is appropriate from the pill box 2001 at that time):

1. The user turns on smart key 2002 and places it on a pill box 2001. The smart key 2002 plastic snaps 2801 engage with pill box 2001.

2. Smart key 2002 uses barcode scanner 2708 to read machine-readable indicia 2003 on pill box 2001 and determines that a dose is necessary at this time, based upon, for example, indicia 2003 that uniquely identifies pill box 2001, the date and time of a previous unlock operation performed on the same pill box 2001 and dosage duration information (e.g., number of hours between dosages). The computing system 2709 uses the identifying indicia 2003 to determine the respective unlock positions of the rotors 2209, such as by a lookup table based on the identifying indicia, performing a hash of indicia 2003, or contacting a remote server. Once the unlock positions are obtained, the processor controls the motors 2704 to rotate rotors 2209 to their respective unlock positions.

3. The user rotates smart key 2002 until it stops, at which point the top cover engaging teeth 2404 will abut against the notch 2403 of rotor rings 2402.

4. Smart key 2002 computing system 2709 uses feedback from sensors 2706, 2707 to recognize that the rotors 2209 are in a rotational position near the top cover engaging teeth 2404 that is sufficient to enable each notch 2403 (in its respective unlocked position) to engage with the corresponding tooth 2404 of the wall 2208, and in response to this signal slowly rotates rotors 2209, such that notches 2403 engage with teeth 2404 and cause smart key 2002 to rotate past these top cover engaging teeth 2404.

5. The user continues to rotate smart key 2002 until it stops rotating, at which point rotor rings 2402 will be pressing up against the next pair of engaging teeth 2404, which is a rotational distance sufficient to expose a single slot 2203 of medicine.

6. The user accesses their dose of medication.

7. Smart key 2002 updates its data store to record the date and time of this unlock operation of pill box 2001, which may be associated with an identifier of pill box 2001, such as read from the machine-readable indicia 2003.

FIGS. 30-40 illustrate yet another embodiment of a medicament dispensing system. The system includes a cartridge 3000 that is typically provided to a patient in the form of a locked and sealed container, such as a locked pill box. A medication manufacturer, pharmacist, or other medication provider can deposit one or many doses of a medication into a container prior to closing and sealing it. The system further includes an unlocking device, referred to occasionally as a smart key 3100, which is typically an electronic device that can be used by the patient to unlock cartridge 3000 at appropriate times and to allow the patient access to a dose of medication. In some embodiments, the smart key 3100 can be used with multiple pill boxes 3000, allowing the patient to use a single smart key 3100 for all of their medication access. Further, the smart key 3100 may be a robust and reusable electronic device, and may be purchased separately by the patient, or it may be provided by an insurance company or an entity overseeing treatment, while the cartridge 3000 itself may be disposable or may be returned to a pharmacy to be refilled and/or reused.

The process for accessing medication using the unlocking device 3100 is referred to occasionally as "unlock and advance." As such, the system typically dispenses medication by first unlocking an internal component of the cartridge and then advancing the component. This process will be explained in more detail below.

Figure 30:
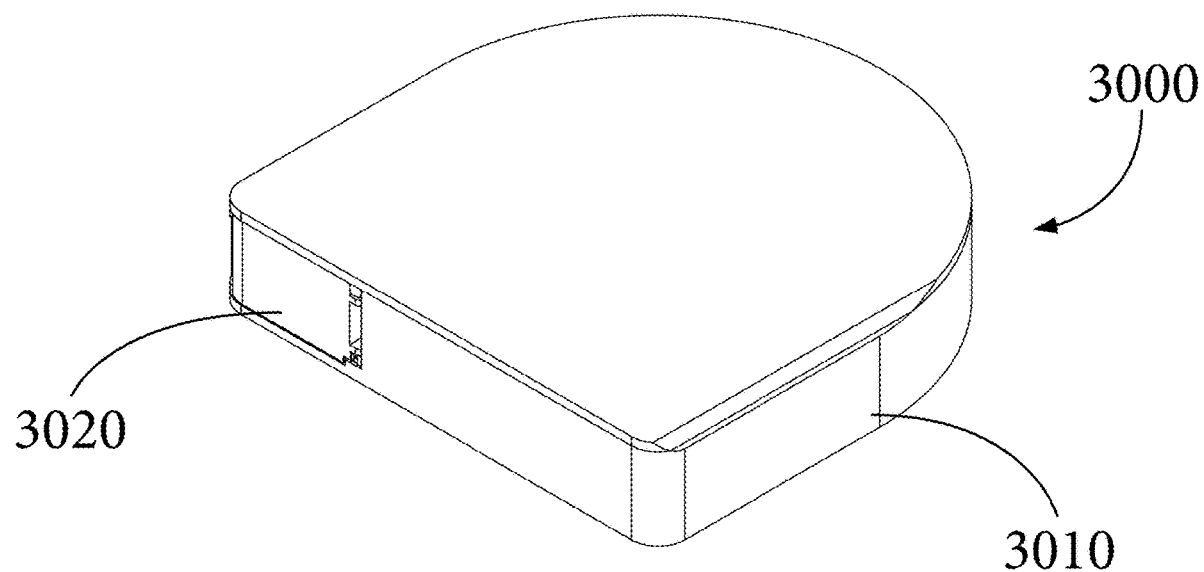
FIG. 30 shows a cartridge for use in an alternate embodiment of a medicament dispensing system.
Figure 31:
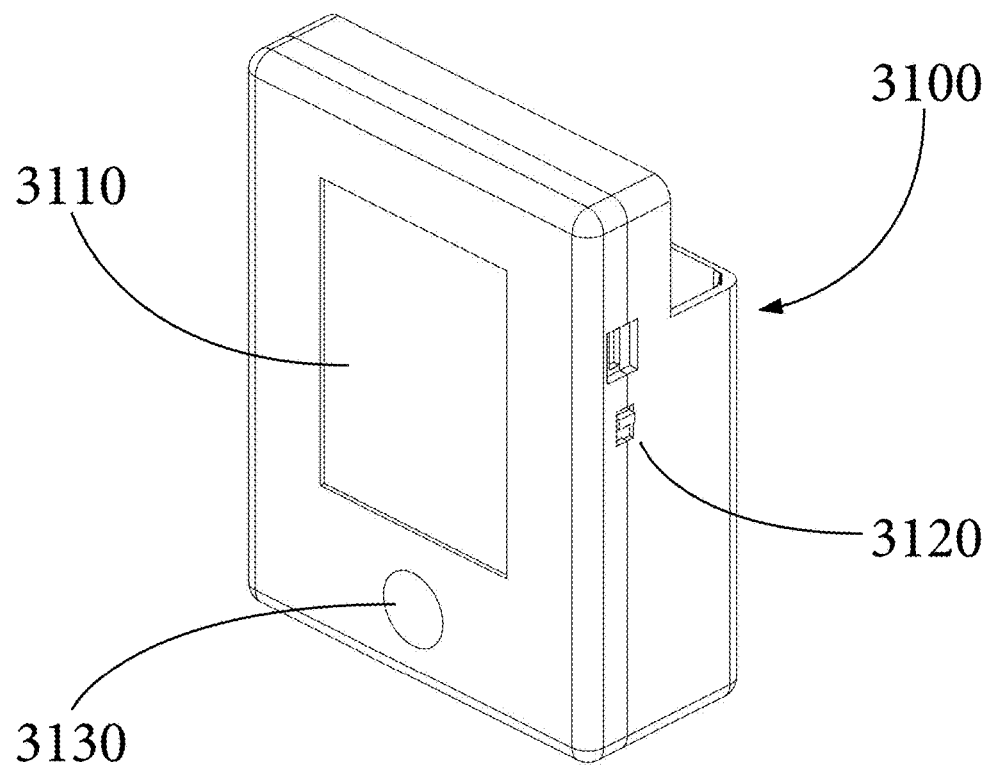
FIG. 31 shows an unlocking device for use with the cartridge shown in FIG. 30.
Figures 32A, 32B:
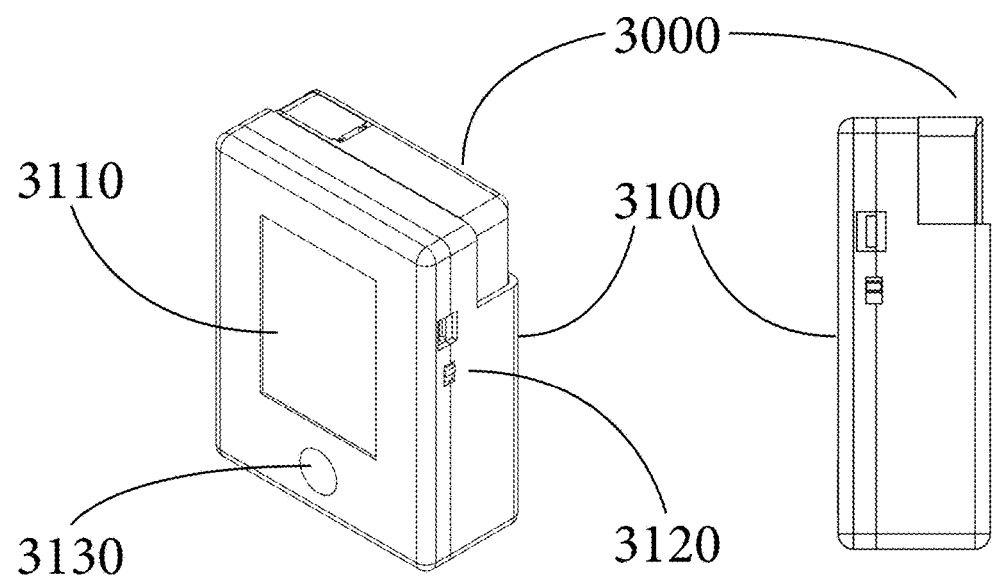
FIGS. 32A-B show the cartridge of FIG. 30 paired with the unlocking device of FIG. 31.

Accordingly, FIG. 30 shows a cartridge 3000 for use in a medicament dispensing system, and FIG. 31 shows an unlocking device 3100 for use with the cartridge. FIGS. 32A and 32B show the cartridge 3000 paired with the unlocking device 3100. As shown, the system typically comprises a lockable cartridge 3000 and an unlocking device 3100 separable from the lockable cartridge that interacts physically with the lockable cartridge. For example, the unlocking device 3100 may have a slot for insertion of the cartridge 3000, as shown, or may be applied to a surface of the cartridge for use as a key.

In use, the unlocking device 3100 provides a motive force for unlocking the lockable cartridge 3000, and upon unlocking the cartridge, a limited amount of a controlled substance, such as a medication, is dispensed from the cartridge. Accordingly, when paired with the cartridge 3000, the unlocking device 3100 applies a force that physically moves an internal component of the cartridge. For example, the unlocking device 3100 may apply a direct force to mechanically interact with the cartridge 3000, thereby unlocking it, or it may apply a magnetic force, as in the embodiment shown, to magnetically manipulate an internal component of the cartridge. Alternatively, the unlocking device 3100 may apply an electromagnetic force to the cartridge 3000 in order to unlock it.

Typically, upon unlocking the cartridge 3000, only a limited amount of the controlled substance is dispensed. This may be, for example, by only providing access to one of several storage compartments within the cartridge 3000. Accordingly, after unlocking the cartridge 3000 to retrieve, for example, one dosage of a medication, the cartridge 3000, or any further storage compartments within the cartridge, remains locked and an additional unlocking action must be taken to access another dosage of the medication.

The cartridge 3000 is provided with a housing 3010, and the unlocking mechanism for the cartridge is within the housing. The unlocking device 3100 is typically required in order to access and manipulate the unlocking mechanism, which is discussed in detail below. As such, the unlocking mechanism is not accessible superficially by a patient at or through the housing 3010, and it cannot be manipulated manually. The housing 3010 of the cartridge 3000 is also typically assembled in a manner that deters access thereto, except as authorized by the unlocking device 3100. Accordingly, it is tamper resistant and typically assembled out of durable and resilient materials. In some embodiments, it may be openable by a pharmacist for reloading purposes using specialized tools, but otherwise remains sealed.

The housing 3010 may have an opening 3020 through which the limited amount of the controlled substance is dispensed when the cartridge 3000 is unlocked.

In some embodiments, the cartridge 3000 may further comprise a data repository containing dispensing instructions for the controlled substance contained therein. In such embodiments, the data repository may be readable by the unlocking device 3100 when paired, as shown in FIG. 32A, B, and may assist the unlocking device in determining if the cartridge should be unlocked.

Figure 33:
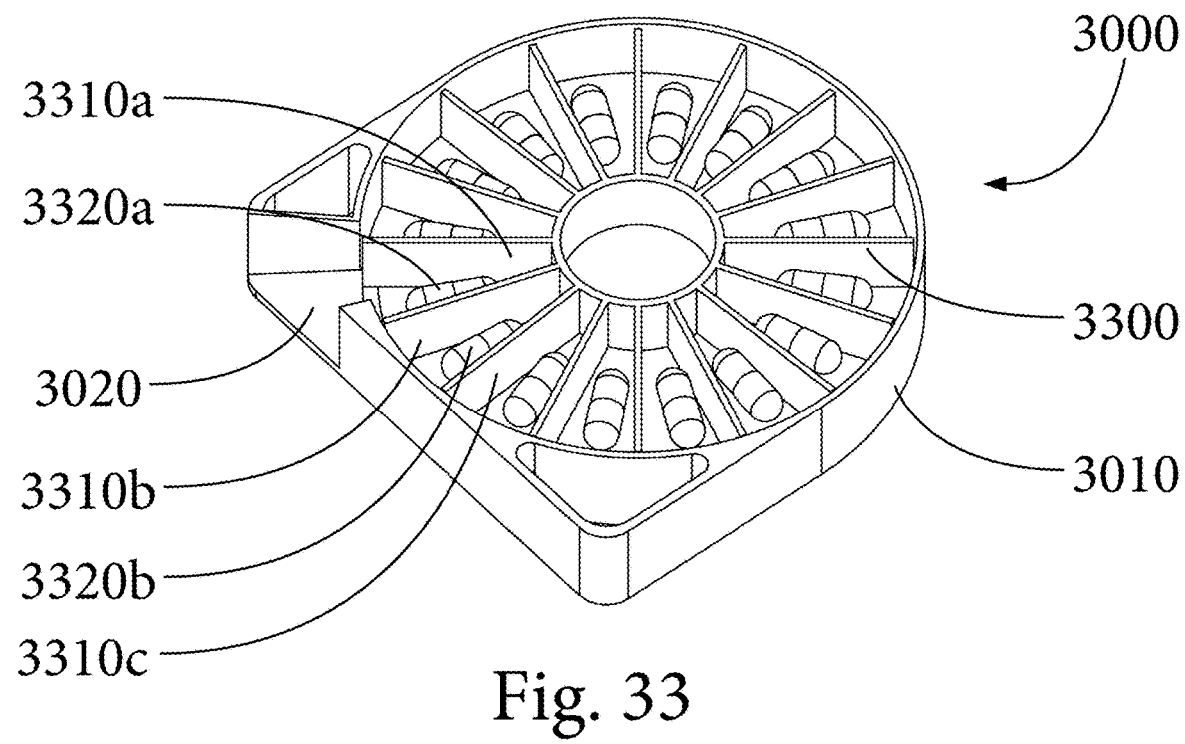
FIG. 33 shows a top perspective view of the cartridge of FIG. 30 with a top portion of an outer housing removed.

FIG. 33 shows a top perspective view of the cartridge 3000 of FIG. 30 with a top portion of an outer housing 3010 removed. As shown, the cartridge 3000 comprises an internal movable part, such as a carousel 3300, which moves within the cartridge in order to provide access to a controlled substance. The carousel 3300 has several storage compartments 3310a, b for storing the controlled substance, here, pills of medication 3320a, b. While the controlled substance is shown as pills, it may be medication in different forms, such as vials or tablets, or in some alternate embodiments, it may be any other product that requires controlled access, such as ammunition for weapons. Accordingly, when the unlocking device 3100 unlocks the cartridge, it may do so by unlocking and advancing the carousel 3300 a single step, corresponding to a single storage compartment 3310.

As shown, each storage compartment 3310 may contain one pill 3320a, b of a medication. During use, one storage compartment 3310a may be aligned with the opening 3020 in the housing 3010 of the cartridge 3000. Accordingly, in its locked state, the storage compartment 3310a aligned with the opening 3020 will be accessible, and after taking the particular dosage of medication 3320a stored in that storage compartment, empty. In unlocking the cartridge, the unlocking device 3100 may then rotate the carousel 3300 in order to align the next storage compartment 3310b with the opening 3020. After the controlled substance 3320b is removed in the next storage compartment 3310b through the opening 3020, the cartridge is once again in a locked state, since the next storage compartment 3310c is inaccessible. In order to rotate the carousel 3300 further, the cartridge 3000 must therefore once again be unlocked using the unlocking device 3100.

While this description is in terms of a carousel 3300, it will be understood that any internal movable part having multiple compartments may be used instead. For example, a conveyor, linear cartridge, or belt having multiple internal storage compartments may be used.

Figure 34:
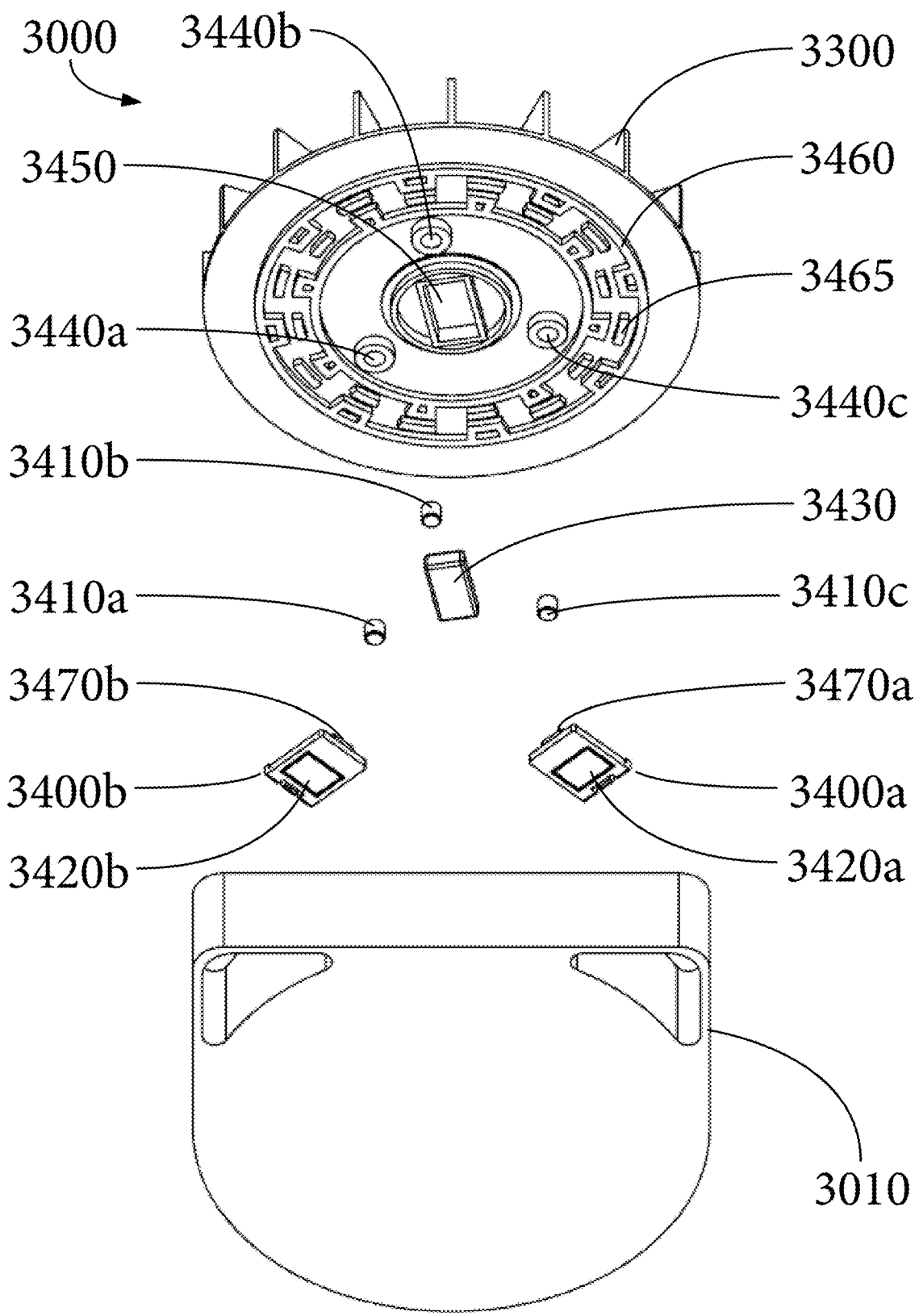
FIG. 34 shows a bottom perspective exploded view of the cartridge of FIG. 30.
Figure 35:
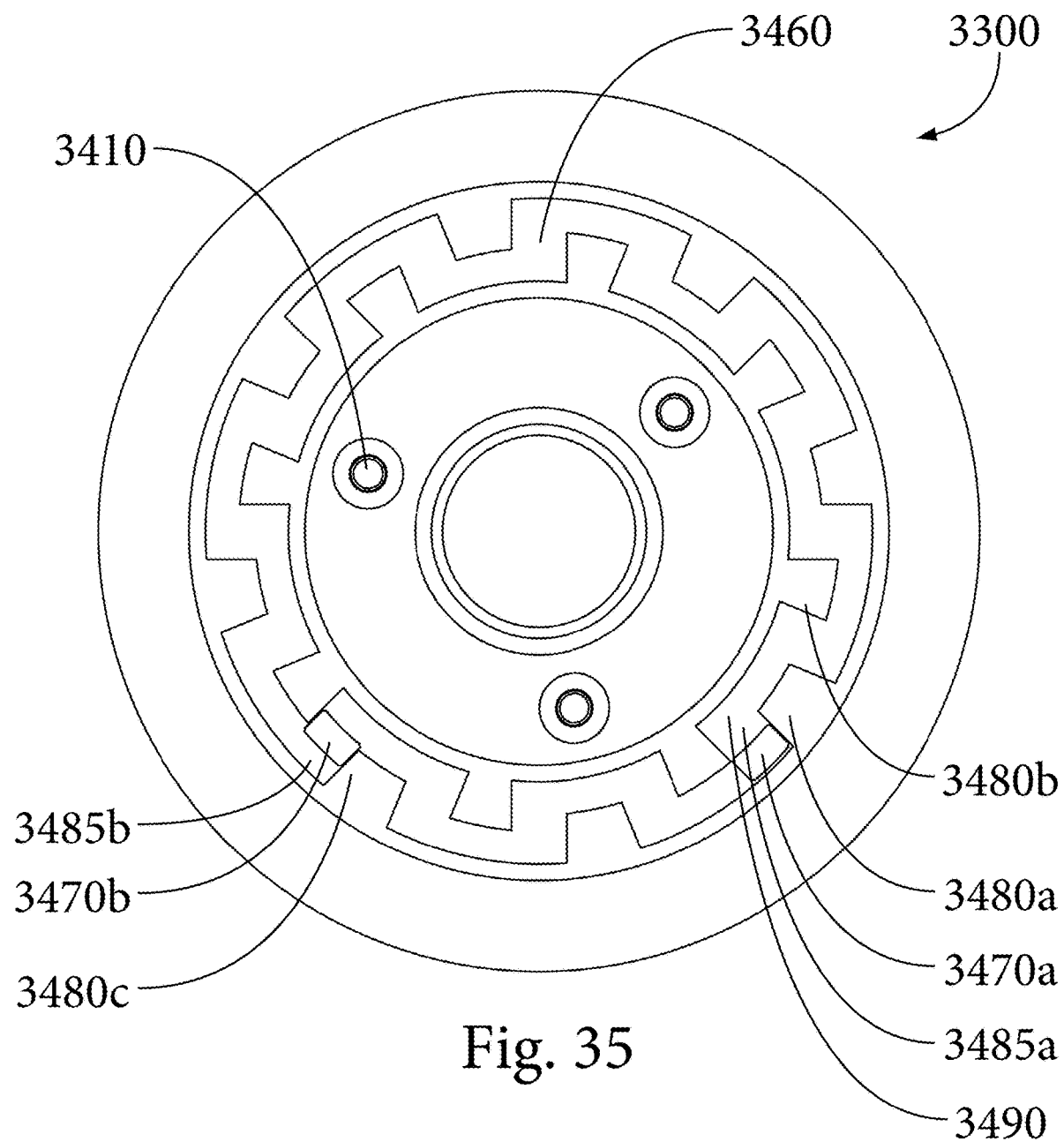
FIG. 35 shows a simplified bottom view of an internal component of the cartridge of FIG. 30.

FIG. 34 shows a bottom perspective exploded view of the cartridge 3000 of FIG. 30, and FIG. 35 shows a simplified bottom view of an internal component, namely the carousel 3300 of the cartridge 3000 of FIG. 30. As shown, the cartridge 3000 comprises the movable part, in the form of carousel 3300, as well as at least one obstruction 3400a, b which functions as a locking mechanism and obstructs the rotation of the carousel. Several magnets, or sets of magnets, 3410a, b, c, 3420a, b are provided for use in manipulating the internal components of the cartridge 3000, with one set 3410 used for rotating the carousel 3300 and the second set 3420 used for manipulating the obstructions 3400. The magnets 3410, 3420 typically interact with corresponding magnets or metal components in the unlocking device 3100. While magnets are shown, they may be replaced with metal components that are manipulated by magnets in the unlocking device 3100, or they may be motorized components controlled electromechanically by the unlocking device.

The cartridge further comprises an additional magnet 3430 for use in detecting an orientation of the carousel 3300. This magnet may be used as a reference point for a sensor, such as a hall-effect sensor inside the unlocking device 3100, for tracking the orientation of the carousel 3300 with respect to the cartridge. Each of the first set of magnets 3410a, b, c is seated at a corresponding fixation point 3440a, b, c on the carousel 3300, and the additional magnet 3430 is located at a known orientation in a corresponding seat 3450 centered on the carousel.

As shown, the bottom surface of the carousel 3300 may be provided with a pattern 3460 for interacting with the obstructions 3400a, b or a pin or extrusion 3470a, b extending from the corresponding obstruction. The pattern 3460 may comprise ridges 3465 and may be embedded in the base of the carousel 3300. The ridges 3465 may be set in a pattern that looks like a maze, with ridges and troughs forming the pattern 3460. The pattern 3460 therefore requires that the extrusion 3470, and therefore the corresponding obstruction 3400, be positioned precisely in order to allow the carousel 3300 to advance. As shown in FIG. 35, one extrusion 3470a is located at a first position in which it abuts one wall 3480a of the pattern 3460, but is unobstructed on its opposite side. Accordingly, the first obstruction 3400a would allow the carousel to rotate counterclockwise, when viewed from the bottom, but not clockwise. The obstruction 3400a may then be moved to second position along a corridor 3485a such that the extrusion 3470a is at a second location 3490 to allow clockwise rotation of the carousel 3300.

Once the extrusion 3470a is moved to the second location 3490, it allows clockwise rotation only until the extrusion 3470a abuts another wall 3480b. Accordingly, the obstruction 3400a may be moved to unlock the cartridge 3000 and advance the carousel 3300 by a single storage compartment 3310, and after that advancement, the cartridge is again locked. In use, the unlocking device 3100 therefore dispenses the controlled substance 3320 by first removing the obstruction 3400a from interfering with rotation by interacting with the corresponding magnets 3420, and then rotating the carousel 3300 by interacting with the corresponding magnets 3410.

In the embodiment shown, the cartridge is provided with a second obstruction 3400b, which is shown in a position such that its extrusion 3470b abuts walls 3480c of the pattern 3460 on both sides. It can then be moved along its own corridor 3485b to either a first location, at which it abuts the wall 3480c only on one side, or it can be moved to a second location, at which it abuts the wall on the opposite side. Typically, the second obstruction 3400b would be moved by the unlocking device 3100 in parallel with the first obstruction 3400a. In some embodiments, only a single obstruction is provided. However, the optional requirement that two or more components internal to the cartridge 3000 be moved in parallel make the locking mechanism more resistant to tampering.

As shown, the pattern 3460 may have a number of corridors 3485 that parallels the number of storage compartments 3310 in the carousel 3300. Accordingly, each movement of the obstruction 3400 along with the corresponding rotation of the carousel 3300 will advance the carousel by one storage compartment 3310.

In some embodiments, a more sophisticated pattern 3460 may be provided, such that the obstruction 3400 may have more than two functional positions. Accordingly, in one example, the movement of the obstruction 3400 from a first position to a second position allows the carousel 3300 to rotate a first limited amount, such as advancing a single storage compartment 3310, and movement of the obstruction from the first position to a third position allows the carousel 3300 to move a second limited amount, such as two storage compartments. In such an embodiment, the unlocking device 3100 may be programmed to release either a single or double dosage at a time, and may move the obstruction accordingly.

Figure 36:
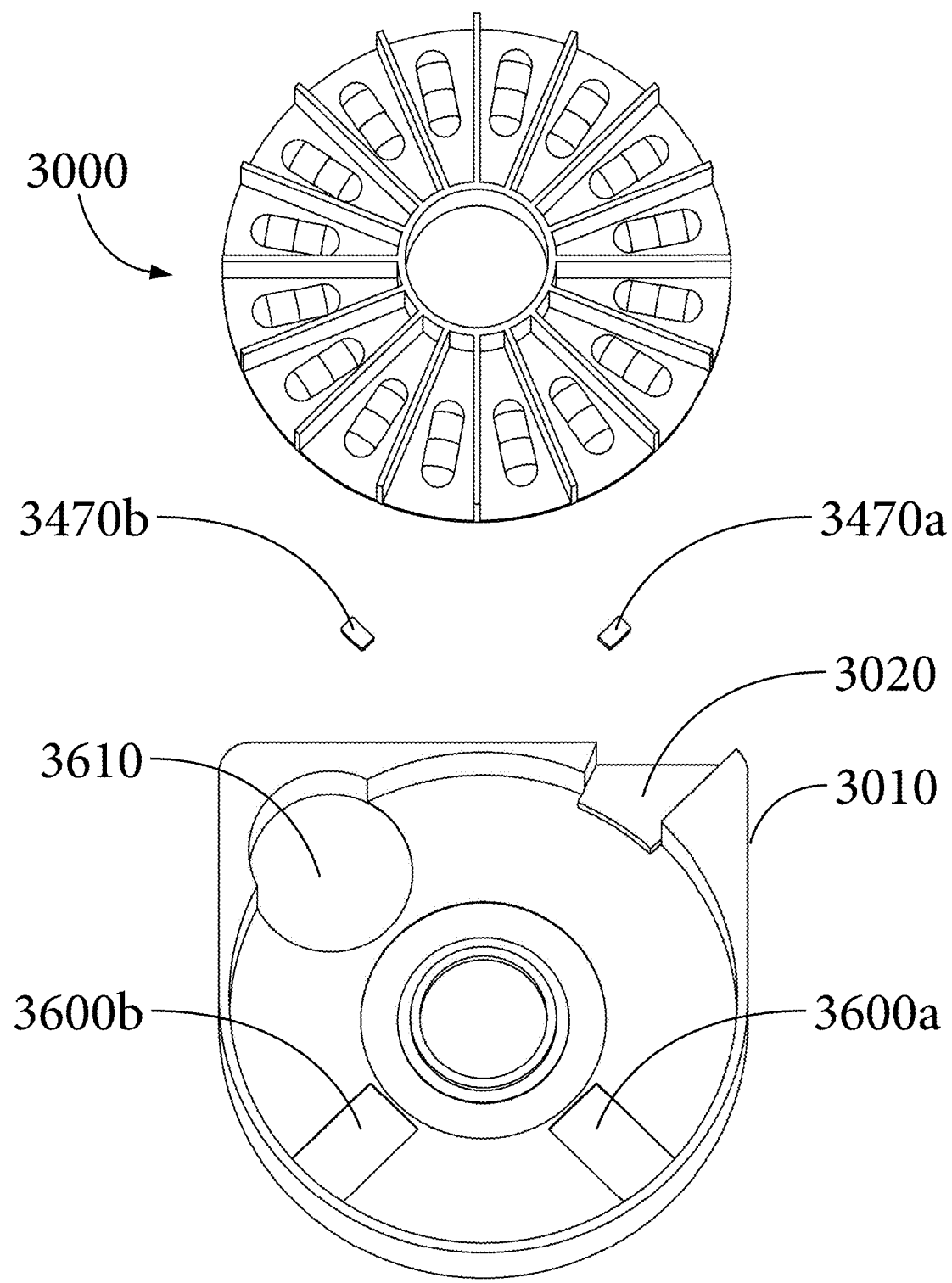
FIG. 36 shows a top perspective exploded view of the cartridge of FIG. 30 with a top portion of the outer housing removed.

FIG. 36 shows a top perspective exploded view of the cartridge 3000 of FIG. 30 with one side of the outer housing 3010 removed. As shown, an interior surface of the opposite side of housing 3010 may have cutouts 3600a, b for locating the corresponding obstructions 3400a, b so that they can slide. The housing 3010 may have further cutouts for locating other components, such as a location 3610 for locating a data repository (not shown). The data repository could be in the form of an RFID tag, or some other storage device that can be read by the unlocking device 3100. The cartridge 3000 can then be labeled, by imparting data to the data repository, with information readable to the unlocking device 3100 such as an identification number, prescription information, etc. Other forms of data repositories or tags would also suffice, so long as alternative mechanisms would be readable by the unlocking device 3100 or through the use of an intermediating technology available to the user, such as a mobile phone.

Figure 37:
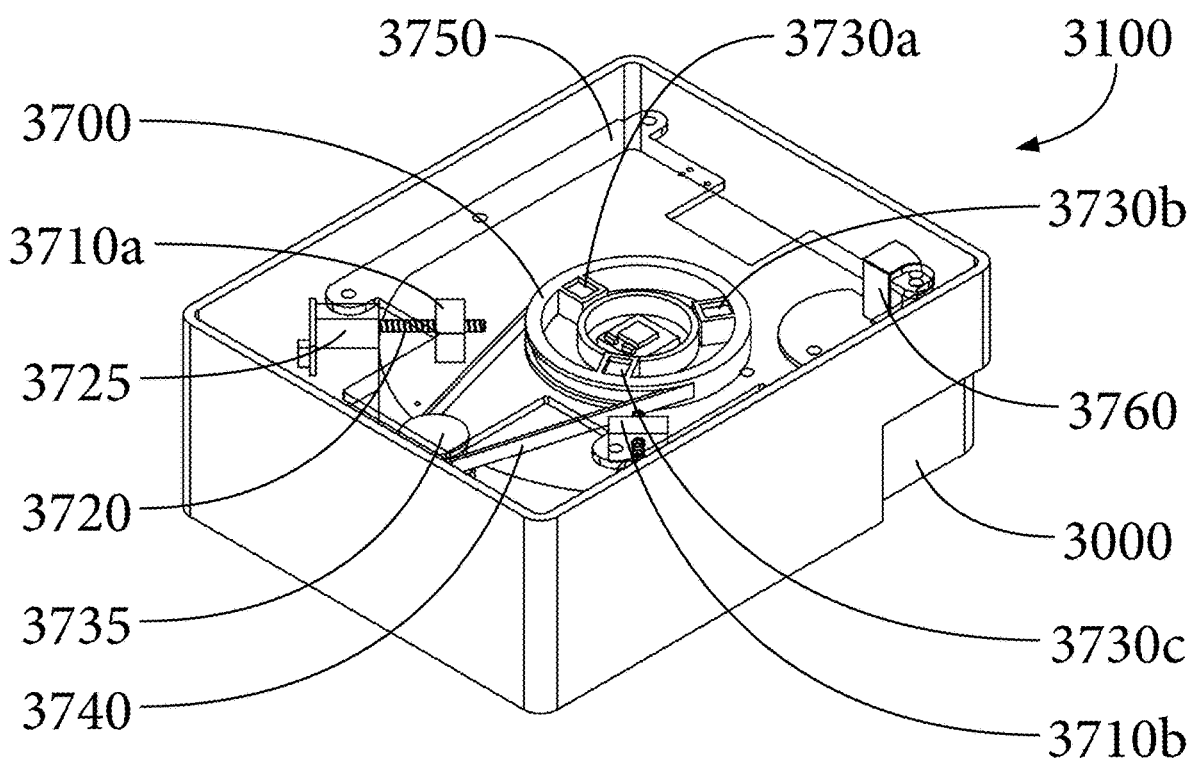
FIG. 37 shows a perspective view of the unlocking device of FIG. 31 with a portion of the outer housing removed.

FIG. 37 shows a perspective view of the unlocking device 3100 of FIG. 31 with a portion of the outer housing removed. As shown, the unlocking device has a rotating element 3700 that interacts with the magnets 3410 of the carousel 3300 and linear elements 3710a, b, that interact with the magnets 3420 of the obstructions 3400. In use, each of the linear elements 3710 are translated using a lead screw 3720 connected to a motor 3725 and the elements interact magnetically to apply a motive force to remove the obstructions 3400 within the cartridge 3000, that is, to position them so that they are not obstructing rotation of the carousel 3300. The rotating element 3700 is then driven by a motor 3735 and a belt 3740 to interact magnetically and apply a motive force to rotate the carousel 3300. It will be understood that while specific motor implementations are shown, additional mechatronic components are contemplated.

Accordingly, the rotating element 3700 has driving magnets 3730a, b, c that interact with corresponding magnets 3410a, b, c on the carousel 3300. The linear elements 3710a, b, each have driving magnets (not shown) that interface with the corresponding magnets of the obstructions 3420a, b.

Figure 38:
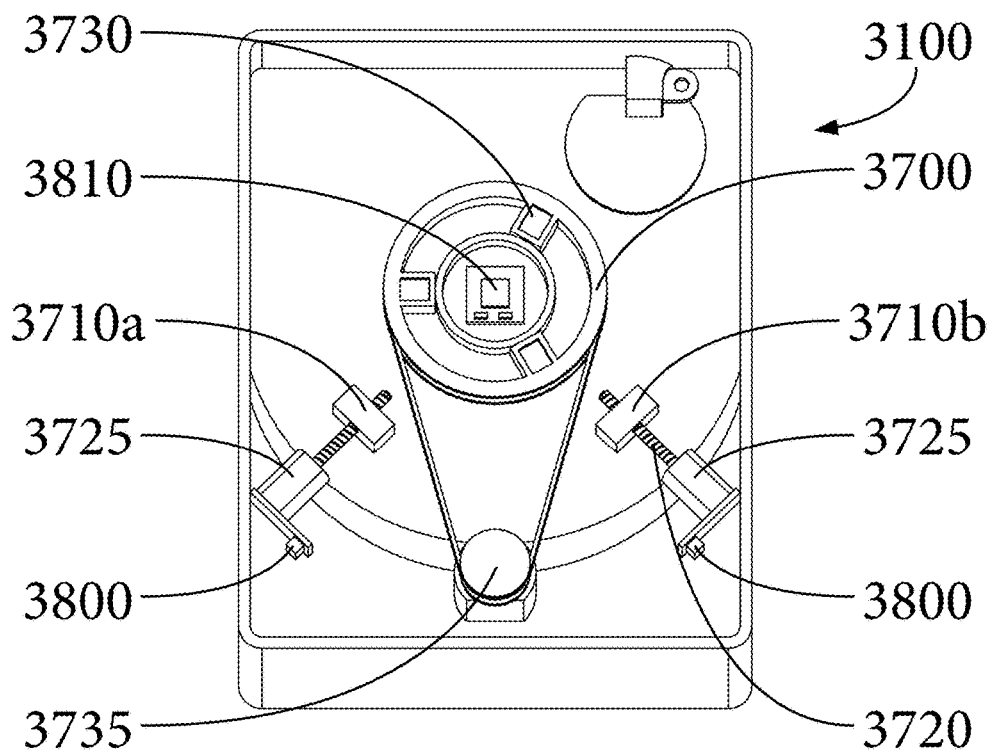
FIG. 38 shows a top perspective view of the unlocking device of FIG. 31 with the portion of the outer housing removed.

FIG. 38 shows a top perspective view of the unlocking device 3100 of FIG. 31 with the portion of the outer housing removed from a different perspective than FIG. 37. As shown, each of the linear elements 3710 contains a driving magnet and is mounted on a lead screw 3720 driven by a corresponding motor 3725. The driving magnets 3730 for the carousel 3300 are in turn mounted on the rotating element 3700 and driven by the drive belt 3740.

Control and monitoring of these various driving magnets such as 3730 and those located as part of linear elements 3710 is accomplished with the assistance of position sensors 3800 that monitor the position of the block driving magnets, and an angular Hall-effect sensor 3810 that monitors the angular position of the magnet 3430 that is mounted on the carousel.

The sensors 3800, 3810 and motors 3725, 3735 are connected to control electronics nested around the mechanical systems. FIG. 37 shows the electronic control board 3750, which typically includes a microprocessor, memory, a wireless modem, and a wireless Bluetooth subsystem for connectivity with a mobile phone. The electronic system may also include connections for input and output to and from the active components, such as sensors 3800, 3810 and motors 3725, 3730 for the driving magnets, and support for biometric authentication via fingerprint scanning. The electronic control board 3750 may also be connected to an NFC reader 3760. The control board typically also controls, and receives information from, a user interface. Accordingly, the board 3750 may control a display, such as a display 3110 and any interface buttons or switches 3120. In the embodiment shown, the display 3110 is a touchscreen, and controls most interface features, and the switch 3120 is an "on/off" switch, as shown in FIG. 31. In the embodiment shown, a fingerprint scanner 3130 is also provided in order to authenticate a user of the unlocking device 3100.

Figure 39:
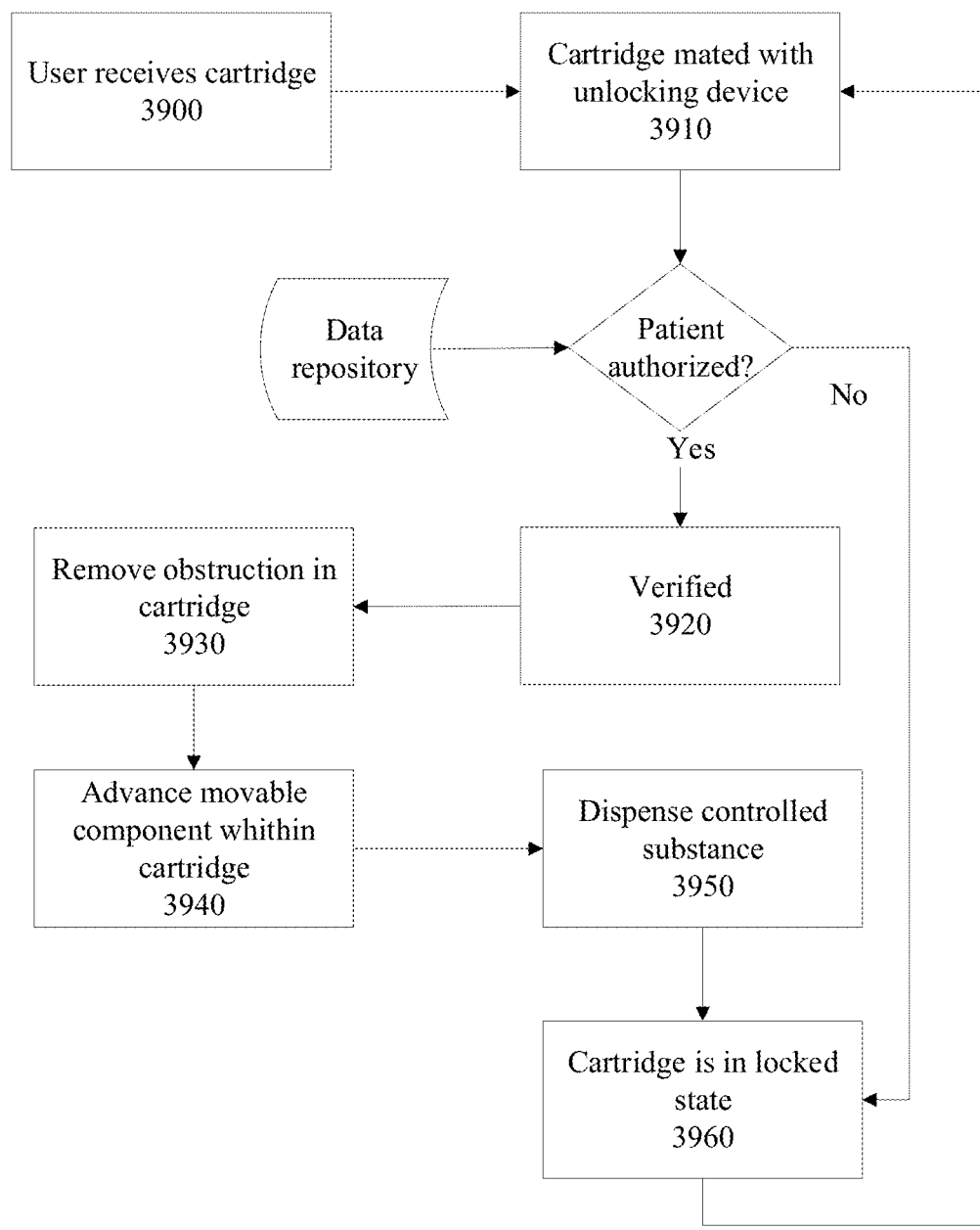
FIG. 39 is a flowchart showing a method for using the system of FIGS. 30-38.

FIG. 39 is a flowchart illustrating a method for using the system shown in FIGS. 30-38. The system is typically used in order to access preloaded medication. Accordingly, the cartridge 3000 is first provided to a user, such as a patient, preloaded with the controlled substance, typically medication 3320 (at 3900). The patient separately acquires the unlocking device 3100, either as a separate purchase or upon the first time they receive a cartridge 3000. At an appropriate time, such as when it is time for a dosage of medication, the cartridge 3000 is then inserted into the unlocking device 3100, and the user interface 3110, 3120, 3130 is used by the user to request access to the medication 3320 (3910).

In some embodiments, the insertion of the cartridge 3000 into the unlocking device is treated as a request for the dispensing of medication 3320. In other embodiments the user interface must be used to request the medication, or the unlocking device dispenses medication 3320 on a predetermined schedule. The unlocking device then confirms (at 3920) that the patient is authorized to extract the medication 3320 at that time. In some embodiments, this may be by reading a data repository within the cartridge 3000 or otherwise verifying data.

Accordingly, if the user is not authorized to access medication 3320 at a particular time, the cartridge 3000 may remain locked (at 3960) and the unlocking device 3100 may be programmed to deny access. For example, if a user requests medication at a rate that exceeds medical guidance, such a request could be denied. The unlocking device 3100 can also be programmed to require a passcode, such as a code known only to the patient authorized to use the device, or to use biometric markers as a passcode, such as via the fingerprint scanner 3130 shown in FIG. 31, such that only a recognized and authorized user can access medication from a cartridge. It will be understood that alternative biometric systems, such as retinal scanning, or other security systems could be implemented as well.

The unlocking device 3100 then applies a first motive force, in the form of magnetically removing an obstruction 3400 (3930), followed by a second motive force, in the form of magnetically moving a movable component 3300 within the cartridge 3000 (3940).

After applying these two forces, the carousel is advanced by one storage compartment 3310 and a pill 3320 is dispensed from the opening 3020 in the housing 3010 (3950). The cartridge then automatically remains in its locked position (3960) until it is once again mated with the unlocking device at 3910 or access is requested to the medication by the user.

Figure 40:
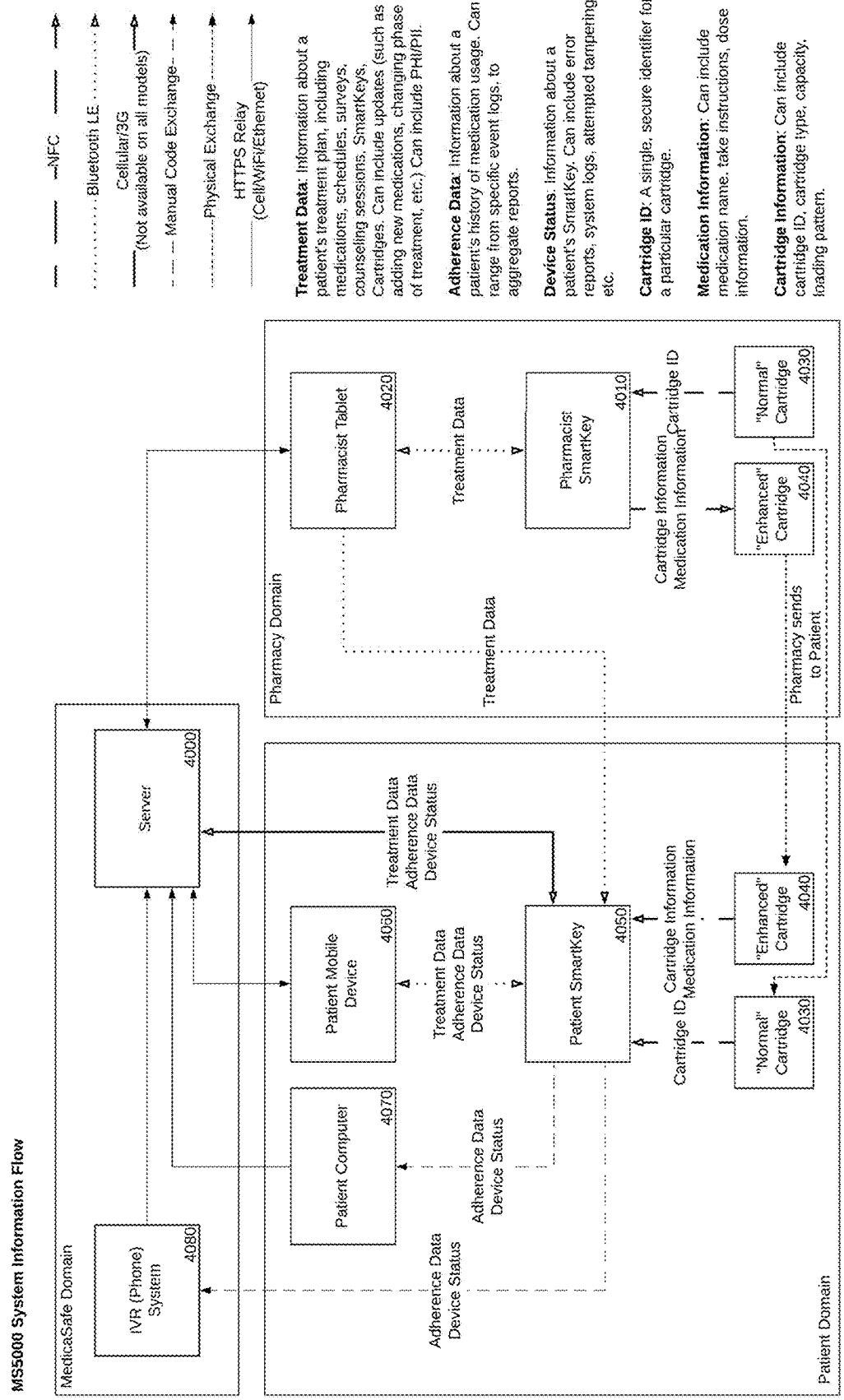
FIG. 40 shows a system diagram for the alternative embodiment of the medicament system comprising the cartridge of FIG. 30 and the unlocking device of FIG. 31.

FIG. 40 shows a system diagram for the alternative embodiment of the medicament system comprising the cartridge 3000 of FIG. 30 and the unlocking device 3100 of FIG. 31. The unlocking device 3100 and cartridge 3000 may be components of a more comprehensive therapy management and monitoring system as shown in FIG. 40. The system may include a server 4000 that serves as a master controller, into which information is provided about patients, prescriptions, cartridges, unlocking device settings, treatment rules, etc. The server 4000 typically would have a data repository, a computing processor, and communication systems. The server 4000 may take advantage of state-of-the-art features in each of those domains. Authorized users can interact with the server 4000 via a remote computing device that has data connectivity with the Server.

The server 4000 can then assemble information to write to a cartridge 3000 NFC tag via an intermediate NFC tag writer. The NFC tag-writer can be a incorporated into a version of the unlocking device 3100 empowered with "NFC-write" functionality and referred to as a pharmacist unlocking device or a pharmacist SmartKey 4010. Interaction with the pharmacist unlocking device 4010 can be facilitated by a tablet 4020 with connectivity to both the server 4000 and the pharmacist unlocking device 4010. The tablet 4020 would typically be provided with a user interface that facilitates the specifying of prescription parameters.

NFC writing may happen when a pharmacist is loading the cartridge 3100 for dispensing, or it may happen when a batch of cartridges are loaded in a wholesale manner for eventual dispensing by a retail pharmacist. The information written to the NFC tag for a normal cartridge 4030 would typically include the medication name, dose strength, and count of the medication loaded into the cartridge. More information may be written to the NFC tag prior to retail dispensing to create an enhanced cartridge 4040, with the enhanced information including the name of the authorized patient, information about the prescribed dosing pattern, any proscribed limits of use, specification of a specific unlocking device allowed to dispense the medication, etc. Prescription parameters can be transmitted to the Server 4000 by the tablet 4020, or via another connected computing device.

The unlocking device 4050 may be provided with networking components, and the server 4000 may then be able to provide instructions to an unlocking device 4050, or monitor the activity of the unlocking device, via any available data communication path, such as transmitting the information wirelessly via a wireless modem. A robust data connection enables the unlocking device 4050 to transmit information to the server 4000 about various issues, such as the exact times that a patient dispensed each dose of the medication 3320. A wireless modem in some embodiments of the unlocking device 3050 enables frequent syncing of information directly between the server and the device, so long as connectivity is available. Other data paths are contemplated as well, such as connecting the unlocking device 4050 to an internet-connected mobile phone 4060 or another computing device 4070. The Server can also generate codes that can be manually entered into the unlocking device 4050 to inform its rules and instructions. Additionally, as noted above, the server 4000 can impart information to the NFC tag of an enhanced cartridge 4040 via an unlocking device 3100 that has 'NFC-write' capability, such as the pharmacist unlocking device 4010. Any such information on the NFC tag can be read by an unlocking device 3100 when the cartridge is inserted and that information can include instructions such as the target dispensing rate, limits of use, etc.

The salient events that the unlocking device 4050 senses or initiates, such as release of medications 3320, may be recorded in the unlocking device 3100 memory and may also be written to the NFC tag of a cartridge 3000. Some or all of this information may eventually be transmitted from the unlocking device 3100 to the server 4000, via any available data communication path, when viable. If data connectivity is not available, information can be transmitted by return of the cartridge 3100 to a clinician that has means to read the NFC tag. The system also supports code-passing, meaning that status codes generated by the unlocking device 3100 can be relayed to the server 4000 and decoded by the server to unpack information. The phrase 'code passing' refers to the technique of embedding information into a code, such as a seemingly random number, such that the device receives that code and decode information from it. In the example embodiment, a status code on the unlocking device 3100 is be algorithmically created such that is contains information about the dispensing pattern of the patient, and any tampering events. The algorithm encrypts this information into the code, and the server 4000 is programmed to decrypt the status code and extract the relevant information. The server 4000 then generates and relays a response code to the patient, which the patient is instructed to enter into the unlocking device 3100. The response code, generated algorithmically and seemingly randomly, can carry information to the unlocking device 3100 to continue or discontinue medication access, maintain or alter access rules, etc. Code-passing can be accomplished by the patient on their internet-connected phone 4060, another internet-connected computing device 4070, or via other known communications means such as an Interactive Voice Response (IVR) system 4080. In some embodiments, a code may be generated and provided to a patient by means of, for example, a key fob or smartphone app, so that it can be manually entered into the unlocking device 3100.

Those skilled in the art will recognize that the present invention has many applications, may be implemented in various manners and, as such is not to be limited by the foregoing embodiments and examples. Any number of the features of the different embodiments described herein may be combined into a single embodiment, the locations of particular elements can be altered and alternate embodiments having fewer than or more than all of the features herein described are possible. Functionality may also be, in whole or in part, distributed among multiple components, in manners now known or to become known.

It will be appreciated by those skilled in the art that changes could be made to the embodiments described above without departing from the broad inventive concept thereof. For example, the above embodiments are discussed with respect to optical readers and optically-readable indicia, as well as an embodiment with radio-frequency identification (RFID) readers in combination with RFID tags. It will be appreciated, however, that other forms of readers and machine-readable indicia can be used, such as magnetic readers in combination with magnetically-encoded media, or the like. It is understood, therefore, that this invention is not limited to the particular embodiments disclosed, but it is intended to cover modifications within the spirit and scope of the present invention. While there has been shown and described fundamental features of the invention as applied to being exemplary embodiments thereof, it will be understood that omissions and substitutions and changes in the form and details of the disclosed invention may be made by those skilled in the art without departing from the spirit of the invention. Moreover, the scope of the present invention covers conventionally known, future developed variations and modifications to the components described herein as would be understood by those skilled in the art.

What is claimed is:

1. A system for controlling access to a controlled substance comprising:
a lockable cartridge having a plurality of internal configurations and a movable part for allowing access to the controlled substance; and
an unlocking device separable from the lockable cartridge that interacts physically with the lockable cartridge to transition the lockable cartridge between the plurality of internal configurations,
wherein the unlocking device provides a motive force for unlocking the lockable cartridge by transitioning the lockable cartridge between the plurality of internal configurations to a first of the internal configurations; and wherein, upon unlocking the lockable cartridge with the unlocking device the movable part is movable a limited amount, and a limited amount of a controlled substance is made accessible from the cartridge by moving the movable part, wherein once moved the limited amount the movable part is obstructed, and wherein once obstructed, the lockable cartridge remains locked until the unlocking device provides a further motive force to transition the lockable cartridge to an internal configuration of the plurality of internal configurations other than the first of the internal configurations.

2. The system of claim 1, wherein the unlocking device provides a first motive force for transitioning the lockable cartridge between the plurality of internal configurations and a second motive force for moving the movable part.

3. The system of claim 2, wherein the movable part has a plurality of storage compartments for storing limited amounts of the controlled substance, and wherein transitioning the lockable cartridge between the plurality of internal configurations and moving the movable part provides access to at least one of the plurality of storage compartments.

4. The system of claim 1, wherein each of the plurality of internal configurations is defined by a position of an obstruction for obstructing the movement of the movable part, and upon removal of the obstruction from a first position defining the first of the plurality of internal configurations to a second position defining a second of the plurality of internal configurations, the movable part can move a limited amount before being obstructed by the obstruction at its second position.

5. The system of claim 1, wherein the movable part is a carousel internal to the lockable cartridge, and wherein each of the plurality of internal configurations limits or prevents rotation of the carousel.

6. The system of claim 5, wherein each of the plurality of internal configurations locates at least one obstruction such that the obstruction interacts with a pattern on a surface of the carousel.

7. The system of claim 1, wherein the unlocking device determines an actual orientation of the movable part using a magnetic sensor.

8. The system of claim 1, wherein the unlocking device interacts magnetically or electro-magnetically with the cartridge.

9. The system of claim 1, wherein upon unlocking the lockable cartridge and making accessible the limited amount of the controlled substance, the lockable cartridge is locked, and must be unlocked again to provide access to dispense additional of the controlled substance.

10. The system of claim 1, wherein the unlocking device is portable and separable from the cartridge, and wherein the cartridge is disposable.

11. The system of claim 1, the lockable cartridge further comprising a housing, and wherein a locking mechanism of the lockable cartridge is not accessible superficially at the housing.

12. The system of claim 1, wherein the unlocking device further comprises a computing system for determining whether access to the controlled substance should be provided.

13. The system of claim 1, the lockable cartridge further comprising a data repository containing dispensing instructions readable by the unlocking device.

14. A lockable cartridge for controlling access to a controlled substance comprising:
a movable part for allowing access to the controlled substance; and
a plurality of internal configurations for limiting or preventing movement of the movable part,
wherein movement of the movable part enables access to a limited amount of the controlled substance, and
wherein upon transitioning the cartridge from a first of the plurality of internal configurations to a second of the plurality of internal configurations, the movable part is movable a limited amount prior to being obstructed, and once obstructed in the second internal configuration, the cartridge must be transitioned to the first internal configuration or a third of the plurality of internal configurations prior to moving the movable part.

15. The lockable cartridge of claim 14 wherein the movable part has a plurality of storage compartments for storing limited amounts of the controlled substance, and wherein transitioning the cartridge from the first internal configuration to the second internal configuration allows movement of the movable part to provide access to at least one of the plurality of storage compartments.

16. The lockable cartridge of claim 14 wherein, each of the plurality of internal configurations is defined by a position of an obstruction for obstructing the movement of the movable part, and upon removal of the obstruction from a first position defining the first of the plurality of internal configurations to a second position defining the second of the plurality of internal configurations, the movable part can move a limited amount before being obstructed by the obstruction at its second position.

17. The lockable cartridge of claim 16 wherein the movable part is a carousel internal to the lockable cartridge, and wherein the obstruction is a barrier preventing rotation of the carousel.

18. The lockable cartridge of claim 14 wherein upon unlocking the lockable cartridge by transitioning the cartridge from the first internal configuration to the second internal configuration and enabling access to the limited amount of the controlled substance, the lockable cartridge is locked, and must be unlocked again to enable access to additional of the controlled substance.

19. The lockable cartridge of claim 16 further comprising a housing, wherein the obstruction is not accessible superficially at the housing.

20. The lockable cartridge of claim 19, wherein the obstruction is movable magnetically.

21. An unlocking device for controlling access to a controlled substance comprising:
a computing system for determining whether access to the substance is to be provided;
an actuator for applying an unlocking motive force to unlock a cartridge containing the substance and a dispensing motive force distinct from the unlocking motive force for moving an internal component of the cartridge,
wherein upon a first determination by the computing system that access to the substance is to be provided by the computing system, the actuator applies a first iteration of the unlocking motive force and the dispensing motive force sequentially to enable access to a limited amount of the controlled substance, and wherein upon a second determination by the computing system that access to the substance is to be provided by the computing system, the actuator applies a second iteration of the unlocking motive force and the dispensing motive force sequentially, and wherein the second iteration of the unlocking motive force differs from the first iteration of the unlocking motive force.

22. The unlocking device of claim 21, wherein each iteration of the unlocking motive force removes an obstruction preventing movement of a movable part internal to the cartridge.

23. A method for controlling access to a controlled substance, the method comprising:
providing a lockable cartridge containing the controlled substance;
providing an unlocking device that interacts physically with the lockable cartridge;
applying at least one motive force to the lockable cartridge using the unlocking device to transition the lockable cartridge between a plurality of internal configurations thereby enabling a movable part in the lockable cartridge to move and enable access to a limited amount of the controlled substance,
wherein the movement of the movable part provides access to the limited amount of the controlled substance, and wherein the movable part moves until obstructed, and
applying the at least one motive force to the lockable cartridge using the unlocking device to again transition the lockable cartridge between the plurality of internal configurations thereby enabling the movable part to again move until obstructed and provide access to an additional limited amount of the controlled substance.

24. The method of claim 23 wherein the at least one motive force is applied magnetically.

* * * * *